US011224660B2

(12) United States Patent
Vangara et al.

(10) Patent No.: US 11,224,660 B2
(45) Date of Patent: Jan. 18, 2022

(54) STABLE CANNABINOID FORMULATIONS

(71) Applicant: RADIUS PHARMACEUTICALS, INC., Boston, MA (US)

(72) Inventors: Kiran Kumar Vangara, Phoenix, AZ (US); Huaguang Li, Chandler, AZ (US); Ningxin Yan, Chandler, AZ (US); Hung Q. Nguyen, Chandler, AZ (US); Venkat R. Goskonda, Phoenix, AZ (US)

(73) Assignee: RADIUS PHARMACEUTICALS, INC., Boston, MA (US)

( * ) Notice: Subject to any disclaimer, the term of this patent is extended or adjusted under 35 U.S.C. 154(b) by 0 days.

(21) Appl. No.: 14/724,351

(22) Filed: May 28, 2015

(65) Prior Publication Data

US 2015/0343071 A1 Dec. 3, 2015

Related U.S. Application Data

(60) Provisional application No. 62/154,660, filed on Apr. 29, 2015, provisional application No. 62/004,495, filed on May 29, 2014.

(51) Int. Cl.
| | | |
|---|---|---|
| *A61K 47/44* | (2017.01) | |
| *A61K 47/22* | (2006.01) | |
| *A61K 47/10* | (2017.01) | |
| *A61K 47/14* | (2017.01) | |
| *A61K 31/05* | (2006.01) | |
| *A61K 31/352* | (2006.01) | |
| *A61K 9/08* | (2006.01) | |

(52) U.S. Cl.
CPC ............... *A61K 47/44* (2013.01); *A61K 9/08* (2013.01); *A61K 31/05* (2013.01); *A61K 31/352* (2013.01); *A61K 47/10* (2013.01); *A61K 47/14* (2013.01); *A61K 47/22* (2013.01)

(58) Field of Classification Search
CPC .......... A61K 47/44; A61K 9/08; A61K 31/05; A61K 31/352; A61K 47/10; A61K 47/14; A61K 47/22
See application file for complete search history.

(56) References Cited

U.S. PATENT DOCUMENTS

| | | |
|---|---|---|
| 2005/0266108 A1 | 12/2005 | Flockhart et al. |
| 2006/0167283 A1 | 7/2006 | Flockhart et al. |
| 2009/0181080 A1* | 7/2009 | Kottayil ............... A61K 9/0014 424/456 |
| 2010/0291205 A1 | 11/2010 | Downie et al. |
| 2011/0306660 A1* | 12/2011 | Goskonda ............ A61K 9/0095 514/454 |
| 2013/0289019 A1 | 10/2013 | Chau |
| 2014/0100269 A1 | 4/2014 | Goskonda et al. |

FOREIGN PATENT DOCUMENTS

| | | |
|---|---|---|
| CN | 1420761 | 5/2003 |
| WO | 200113886 | 3/2001 |
| WO | 2002064109 | 8/2002 |
| WO | 2006063109 | 6/2006 |
| WO | 2009147439 | 12/2009 |

OTHER PUBLICATIONS

Office Action dated Jan. 28, 2021 in connection with CN 201580041466.9.
Office Action dated Aug. 19, 2020 in connection with AU 2015266897.
Office Action dated Jun. 11, 2021 in connection with CA 2,950,424.
European Search Report dated Dec. 15, 2017 in connection with EP 15800669.2.
Office Action dated Jun. 4, 2019 in connection with JP 2016-569911.
Office Action dated Jul. 5, 2021 in connection with IL 249197.
Office Action dated Dec. 3, 2020 in connection with MX/a/2016/015636.
Office Action dated Oct. 10, 2019 in connection with NZ 726746.
Cunha et al.; Chronic administration of cannabidiol to healthy volunteers and epileptic patients, Pharmacology. 1980, 21(3), 175-85.
Pertwee; Cannabidiol as a Potential Medicine, in Cannabinoids as Therapeutics, R. Mechoulam, ed., Birkhauser Verlag, 2005.
Trembly et al.; (1990) Double-blind clinical study of cannabidiol as a secondary anticonvulsant, paper presented at Marijuana '90 Int. Conf. on Cannabis and Cannabinoids, Kolympari (Crete), Jul. 8-11, cited according to: Consroe P, Sandyk R. Potential role of cannabinoid°i for therapy of neurological disorders, in Murphy L. Bartke A, eds. Marijuana/Catmabinoids, Neurobiology and Neurophysiology. CRC Press, 1992, 459-524).
First Office Action with English Translation for Japanese Application No. 2016-569911 dated Mar. 5, 2019.
First Mexican Office Action for MX Application No. MX/A/2016/015636 dated Apr. 10, 2019.
Official Notification for Israeli Application No. 249197 dated Apr. 30, 2019.
Office Action for Japanese Application No. 2016-569911 dated Jun. 4, 2019.
First Office Action with English Translation for Chinese Application No. 201580041466.9 dated Aug. 5, 2019.
Second Mexican Office Action for MX Application No. MX/A/2016/015636 dated Aug. 14, 2019.
Third Mexican Office Action for MX Application No. MX/A/2016/015636 dated Jul. 13, 2020.
Third Office Action with English Translation for Chinese Application No. 201580041466.9 dated Aug. 31, 2020.

* cited by examiner

*Primary Examiner* — Kortney L. Klinkel
*Assistant Examiner* — William Y Lee
(74) *Attorney, Agent, or Firm* — Troutman Pepper Hamilton Sanders LLP

(57) ABSTRACT

The present invention is generally directed to substantially pure cannabidiol, stable cannabinoid pharmaceutical formulations, and methods of their use.

12 Claims, 2 Drawing Sheets

STABLE CANNABINOID FORMULATIONS

PRIORITY

This application claims priority to U.S. Provisional Patent Application Nos. 62/004,495, filed May 29, 2014, and 62/154,660, filed Apr. 29, 2015. The entire contents of each application is incorporated herein by reference.

FIELD OF THE INVENTION

The present invention is generally directed to substantially pure cannabidiol, stable cannabinoid pharmaceutical formulations, and methods of their use.

BACKGROUND

Cannabinoids are chemicals that are produced by cannabis flowers. Cannabinoids imitate endogenous compounds in humans.

Cannabinoids include cannabinol, cannabidiol, dronabinol (delta-9-tetrahydrocannabinol), delta-8-tetrahydrocannabinol, 11-hydroxy-tetrahydrocannabinol, 11-hydroxy-delta9-tetrahydrocannabinol, levonantradol, delta-11-tetrahydrocannabinol, tetrahydrocannabivarin, amandamide, nabilone, and acids and analogs thereof. It is now possible to synthesize many cannabinoids in a laboratory thereby eliminating the need to grow cannabis for extraction of the compounds.

One cannabinoid, cannabidiol, (−)-trans-2-p-mentha-1,8-dien-3-yl-5-pentylresorcinol, is non-psychoactive and has shown promise in treating numerous diseases and disorders. Synthetic cannabidiol has the same structure as naturally occurring cannabidiol.

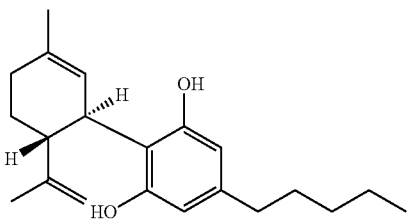 [SMILES: C=C(C)[C@@H]1CCC(C)=C[C@H]1c1c(O)cc(CCCCC)cc1O]

Commercially available cannabidiol is usually contaminated with delta 9-tetrahydrocannabinol. The presence of delta-9-tetrahydrocannabinol can be a concern because delta-9-tetrahydrocannabinol is regulated by the United States Drug Enforcement Administration as a Schedule I Drug. Having a higher Schedule number could result in easier access for patients to cannabidiol treatments. Further, delta-9-tetrahydrocannabinol is a hallucinogen and patients receiving cannabidiol wish to avoid this undesirable side effect of the delta-9-tetrahydrocannabinol contaminant. Therefore, there is a need for a substantially pure synthetically synthesized cannabidiol that does not contain delta-9-tetrahydrocannabinol.

Cannnabinoids, including cannabidiol, may be suitable for the treatment of diseases or disorders, or symptoms of diseases or disorders, such as Dravet Syndrome, Lennox Gastaut Syndrome, mycolonic seizures, juvenile mycolonic epilepsy, refractory epilepsy, schizophrenia, juvenile spasms, West syndrome, refractory infantile spasms, infantile spasms, tubular sclerosis complex, brain tumors, neuropathic pain, cannabis use disorder, post-traumatic stress disorder, anxiety, early psychosis, Alzheimer's Disease autism, and withdrawal from opioids, cocaine, heroin, amphetamines, and nicotine.

Accordingly, there is a need for new stable cannabinoid formulations. There is also a need for substantially pure cannabidiol.

SUMMARY OF THE INVENTION

In one aspect, the present invention is directed to stable pharmaceutical formulations for oral administration comprising from about 0.1 to about 50% of a cannabinoid, from about 0.1 to about 40% of a polyethylene glycol, from about 0.1 to about 50% of propylene glycol, and from about 0.1 to about 20% of water, wherein the formulation does not contain alcohol and the formulation has a pH of from about 5 to about 8.

In another aspect, the present invention is directed to stable pharmaceutical formulations for oral administration comprising from about 0.1 to about 40% of a cannabinoid, from about 0.1 to about 25% of a polyethylene glycol, from about 0.1 to about 40% of propylene glycol, optionally from about 0.1 to about 50% of water; and from about 0.1 to about 70% of alcohol, wherein the formulation has a pH of from about 5 to about 8.

In yet another aspect, the present invention is directed to stable pharmaceutical formulations for oral administration comprising from about 0.1 to about 40% of a cannabinoid and from about 10 to about 95% of a lipid.

In another aspect, the invention is directed to methods of using a cannabinoid or substantially pure, synthetically synthesized cannabidiol: to treat diseases or disorders, or symptoms of diseases or disorders, such as Dravet Syndrome, Lennox Gastaut Syndrome, mycolonic seizures, juvenile mycolonic epilepsy, refractory epilepsy, schizophrenia, juvenile spasms, West syndrome, infantile spasms, refractory infantile spasms, tubular sclerosis complex, brain tumors, neuropathic pain, cannabis use disorder, post-traumatic stress disorder, anxiety, early psychosis, Alzheimer's Disease, and autism; to assist with withdrawal from opioids, cocaine, heroin, amphetamines and nicotine; and as an analgesic or to assist with handling of adverse emotional stimuli.

DETAILED DESCRIPTION

Applicant unexpectedly created new storage stable formulations containing cannabinoids. Applicant determined that a pH of from about 5 to about 8 is critical for the formulations to remain stable, preferably from about 6 to about 7. For example, as seen in Example 2 below, the alcohol-free formulations #AF3 and #AF4 exhibited excellent stability for four weeks regardless of the temperature and humidity conditions. Further, in Example 4, Applicant unexpectedly found that the alcohol containing formulations #A7 and #A8 exhibited excellent stability for at least 12 months regardless of the temperature and humidity conditions. Applicant also determined that an antioxidant is important to maintain stability during long-term storage. These results were not expected because formulation science is incredibly difficult to predict and many otherwise suitable formulations for pharmaceutical use are not stable during storage.

As indicated above, Applicant created stable formulations with and without alcohol (see Examples 1 and 3). The formulations that do not contain alcohol are especially suitable for administration to children. Further, the alcohol-free formulations are especially suitable for patients in recovery from drug and alcohol addiction.

In addition, Applicant created stable formulations lipid formulations (see Example 5). These formulations were also unexpectedly stable during storage (see Example 6).

Figure 1:
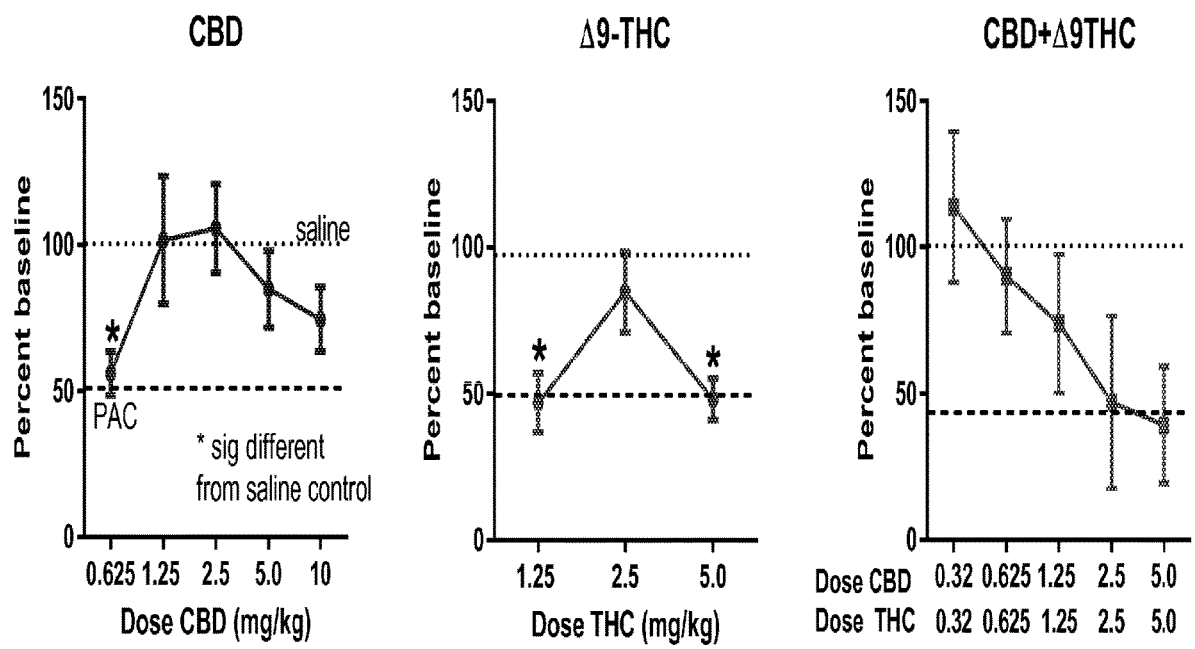
FIG. 1 shows the results from the study detailed in Example 7 and illustrates the advantages of administration of substantially pure, synthetically synthesized, cannabidiol formulations for treatment of neuropathic pain.
Figure 2:
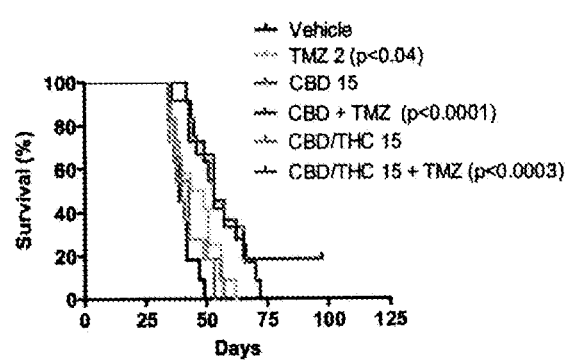
FIG. 2 shows the results from the study detailed in Example 9 and illustrates the advantages of administration of substantially pure, synthetically synthesized, cannabidiol formulations for treatment of glioblastoma multiforme.

Further, Applicant unexpectedly found that substantially pure cannabidiol formulations are especially suitable for treatment of epilepsy (see Examples 8, 10 and 11), neuropathic pain (see Example 7 and FIG. 1), and glioblastoma multiforme (see Example 9 and FIG. 2).

Alcohol-Free Formulations

In one embodiment, the present invention is directed to stable pharmaceutical formulation for oral administration comprising from about 0.1 to about 50% of a cannabinoid, from about 0.1 to about 40% of a polyethylene glycol, from about 0.1 to about 50% of propylene glycol, and from about 0.1 to about 20% of water, wherein the formulation does not contain alcohol and the formulation has a pH of from about 5 to about 8.

In a preferred embodiment, the formulations contain from about 1 to about 40% of a cannabinoid. In more preferred embodiments, the formulations contain from about 5 to about 35%, from about 20 to about 35% or from about 30 to 35% of a cannabinoid.

In yet another embodiment, the formulations contain a cannabinoid selected from group consisting of cannabinol, cannabidiol, dronabinol (delta-9-tetrahydrocannabinol), delta-8-tetrahydrocannabinol, 11-hydroxy-tetrahydrocannabinol, 11-hydroxy-delta-9-tetrahydrocannabinol, levonantradol, delta-11-tetrahydrocannabinol, tetrahydrocannabivarin, amandamide, nabilone, acids, analogs, and synthetic derivatives thereof. In a preferred embodiment, the cannabinoid is cannabidiol.

In a preferred embodiment, the formulations contain from about 1 to about 40% of a cannabidiol. In more preferred embodiments, the formulations contain from about 5 to about 35%, from about 20 to about 35% or from about 30 to 35% of a cannabidiol.

In yet another embodiment, the formulations contain cannabidiol that is substantially pure and synthetically synthesized which has a purity of greater than 98%. In a more preferred embodiment, the cannabidiol is greater than 99% pure. In an even more preferred embodiment, the cannabidiol is greater than 99.5% pure. In a most preferred embodiment, the cannabidiol formulation contains less than 0.3% delta-9-tetrahydrocannabinol.

In another embodiment, the formulations contain from about 0.001 to about 1% of an antioxidant. In a preferred embodiment, the formulations contain from about 0.01 to about 1% antioxidant. In a more preferred embodiment, the formulations contain from about 0.02 to about 0.5% antioxidant.

Suitable antioxidants include butylated hydroxyltoluene, butylated hydroxyl anisole, alpha-tocopherol (Vitamin E), ascorbyl palmitate, ascorbic acid, sodium ascorbate, ethylenediamino tetraacetic acid, cysteine hydrochloride, citric acid, sodium citrate, sodium bisulfate, sodium metabisulfite, lecithin, propyl gallate, sodium sulfate, monothioglycerol and combinations thereof. In a preferred embodiment, the formulations contain alpha-tocopherol (Vitamin E), ascorbic acid, sodium ascorbate, ascorbyl palminate or combinations thereof.

In another embodiment, the formulations contain from about 1 to about 40% of a polyethylene glycol. In a preferred embodiment, the formulations contain from about 1 to about 35%, from about 5 to about 35%, from about 20 to about 30%, or from about 25 to about 30% polyethylene glycol.

Suitable polyethylene glycols include low molecular weight polyethylene glycols with an average molecular weight of between 200 and 10,000. One preferred polyethylene glycol that can be used is polyethylene glycol 400.

In another embodiment, the formulations contain from about 1 to about 40% of polyethylene glycol 400. In a preferred embodiment, the formulations contain from about 1 to about 35%, from about 5 to about 35%, from about 20 to about 30%, or from about 25 to about 30% polyethylene glycol 400.

In another embodiment, the formulations contain from about 1 to about 50% of propylene glycol. In a preferred embodiment, the formulations contain from about 1 to about 40%, from about 5 to about 35%, from about 20 to about 35%, or from about 30 to about 35% propylene glycol.

In a further embodiment, the formulations contain water. The formulations can contain 0% water. If the formulations contain water, they can include from about 1 to about 15% water, from about 1 to about 10% water, or from about 4 to about 8% water.

The pH of the formulations may be modified using any pharmaceutically acceptable means. Preferably the pH of the formulation is from about 5 to about 8. In a more preferred embodiment, the pH of the formulations is from about 6 to about 7. In a most preferred embodiment, the pH of the formulations is from about 6.2 to about 6.7.

The formulations of the present invention may also contain sweeteners, sweetener enhancers, preservatives, pH modifiers, and flavoring agents.

Suitable sweeteners include, but are not limited to, sucrose, aspartame, saccharin, dextrose, mannitol, xylitol, and combinations thereof.

If the formulations contain a sweetener, the formulations preferably contain from about 0.001 to about 1% sweetener.

If the formulations contain a sweetness enhancer, the formulations preferably contain from about 0.001 to about 1% sweetness enhancer.

Suitable sweetness enhancers include, but are not limited to, the ammonium salt forms of crude and refined Glycyrrhizic Acid. Magnasweet® products (available from Mafco Worldwide Corporation, Magnasweet is a registered trademark of Mafco Worldwide Corporation) use the ammonium salt forms of crude and refined Glycyrrhizic Acid. Glycyrrhizic Acid is also available as a pure derivative in the sodium and potassium salt forms.

Suitable pH modifiers include, but are not limited to, hydrochloric acid, ascorbic acid, citric acid, sodium citrate, fumaric acid, sodium hydroxide, sodium bicarbonate, sodium carbonate, ammonium carbonate, and combinations thereof.

Suitable preservatives include, but are not limited to, methyl paraben, propyl paraben, benzyl alcohol, benzoic acid, sodium benzoate, sorbic acid, and combinations thereof.

Suitable flavoring agents include, but are not limited to, raspberry, peppermint oil, grape flavor, menthol, spearmint oil, citrus oil, cinnamon oil, strawberry flavor, cherry flavor, raspberry flavor, orange oil, lemon oil, lemon mint flavor, fruit punch flavor, and combinations thereof. In a preferred embodiment, the formulations contain strawberry flavor.

If the formulations contain a flavoring agent, the formulations preferably contain from about 0.001 to about 1% flavoring agent. In a more preferred embodiment, the formulations contain from about 0.005 to about 0.5% of the flavoring agent.

The formulations are suitable for oral, buccal, sublingual, inhalation or intravenous/intramuscular administration. Preferably, the formulations are liquids administered orally.

Formulations Containing Alcohol

In another embodiment, the invention is directed to stable pharmaceutical formulation for oral administration comprising from about 0.1 to about 40% of a cannabinoid, from about 0.1 to about 25% of a polyethylene glycol, from about 0.1 to about 40% of propylene glycol, optionally from about 0.1 to about 50% of water, and from about 0.1 to about 70% of alcohol, wherein the formulation has a pH of from about 5 to about 8.

In a preferred embodiment, the formulations contain from about 1 to about 35% of a cannabinoid. In a more preferred embodiment, the formulations contain from about 1 to about 15%, from about 5 to about 12% or from about 7 to about 11% cannabinoid. Alternatively, the formulations may contain from about 20 to about 35% or from about 30 to about 35% cannabinoid.

In yet another embodiment, the formulations contain a cannabinoid selected from group consisting of cannabinol, cannabidiol, dronabinol (delta-9-tetrahydrocannabinol), delta-8-tetrahydrocannabinol, 11-hydroxy-tetrahydrocannabinol, 11-hydroxy-delta-9-tetrahydrocannabinol, levonantradol, delta-11-tetrahydrocannabinol, tetrahydrocannabivarin, amandamide, nabilone, acids, analogs, and synthetic derivatives thereof. In a preferred embodiment, the cannabinoid is cannabidiol.

In a preferred embodiment, the formulations contain from about 1 to about 35% of a cannabidiol. In a more preferred embodiment, the formulations contain from about 1 to about 15%, from about 5 to about 12% or from about 7 to about 11% cannabidiol. Alternatively, the formulations may contain from about 20 to about 35% or from about 30 to about 35% cannabidiol.

In yet another embodiment, the formulations contain cannabidiol that is substantially pure and synthetically synthesized which has a purity of greater than 98%. In a more preferred embodiment, the cannabidiol is greater than 99% pure. In an even more preferred embodiment, the cannabidiol is greater than 99.5% pure. In a most preferred embodiment, the cannabidiol formulation contains less than 0.3% delta-9-tetrahydrocannabinol.

In another embodiment, the formulations contain from about 0.001 to about 1% of an antioxidant. In a preferred embodiment, the formulations contain from about 0.01 to about 1% antioxidant. In a more preferred embodiment, the formulations contain from about 0.02 to about 0.5% antioxidant.

Suitable antioxidants include butylated hydroxyltoluene, butylated hydroxyl anisole, alpha-tocopherol (Vitamin E), ascorbyl palmitate, ascorbic acid, sodium ascorbate, ethylenediamino tetraacetic acid, cysteine hydrochloride, citric acid, sodium citrate, sodium bisulfate, sodium metabisulfite, lecithin, propyl gallate, sodium sulfate, and combinations thereof. In a preferred embodiment, the formulations contain alpha-tocopherol (Vitamin E), ascorbic acid, sodium ascorbate, ascorbyl palminate or combinations thereof.

In another embodiment, the formulations contain from about 1 to about 20% of propylene glycol. In a preferred embodiment, the formulations contain from about 1 to about 15% or from about 5 to about 10% propylene glycol.

In an alternative embodiment, the formulations contain from about 20 to about 50% of propylene glycol. In a preferred embodiment, the formulations contain from about 30 to about 40% or from about 30 to about 35% propylene glycol.

In another embodiment, the formulations contain from about 1 to about 20% of a polyethylene glycol. In a preferred embodiment, the formulations contain from about 1 to about 10% or from about 1 to about 5% polyethylene glycol.

In an alternative embodiment, the formulations contain from about 10 to about 20% of a polyethylene glycol. In a preferred alternative embodiment, the formulations contain from about 15 to about 20% polyethylene glycol.

Suitable polyethylene glycols include low molecular weight polyethylene glycols with an average molecular weight of between 200 and 10,000. One preferred polyethylene glycol that can be used is polyethylene glycol 400.

In another embodiment, the formulations contain from about 1 to about 20% of polyethylene glycol 400. In a preferred embodiment, the formulations contain from about 1 to about 10% or from about 1 to about 5% polyethylene glycol 400.

In an alternative embodiment, the formulations contain from about 10 to about 20% of polyethylene glycol 400. In a preferred alternative embodiment, the formulations contain from about 15 to about 20% polyethylene glycol 400.

In a further embodiment, the formulations contain water. The formulations can contain 0% water. If the formulations contain water, they can include from about 1 to about 40% water, from about 5 to about 40% water, from about 10 to about 35% water or from about 25 to about 35% water.

In yet another embodiment, the formulations contain from about 1 to about 65% alcohol. In a preferred embodiment, the formulations contain from about 10 to about 65%, from about 15 to about 60%, or from about 30 to 55% alcohol.

In an alternative embodiment, the formulations contain from about 1 to about 20% alcohol. In a preferred alternative embodiment, the formulations contain from about 1 to about 10% or from about 3 to about 7% alcohol.

The pH of the formulations may be modified using any pharmaceutically acceptable means. Preferably the pH of the formulations is from about 6 to about 7. In a more preferred embodiment, the pH of the formulations is from about 6.2 to about 6.7.

The formulations of the present invention may also contain sweeteners, sweetener enhancers, pH modifiers, preservatives, and flavoring agents.

Suitable sweeteners include, but are not limited to, sucrose, aspartame, saccharin, dextrose, mannitol, xylitol, and combinations thereof.

If the formulations contain a sweetener, the formulations preferably contain from about 0.001 to about 1% sweetener.

Suitable sweetness enhancers include, but are not limited to, the ammonium salt forms of crude and refined Glycyrrhizic Acid. Magnasweet® products (available from Mafco Worldwide Corporation, Magnasweet is a registered trademark of Mafco Worldwide Corporation) use the ammonium salt forms of crude and refined Glycyrrhizic Acid. Glycyrrhizic Acid is also available as a pure derivative in the sodium and potassium salt forms.

If the formulations contain a sweetness enhancer, the formulations preferably contain from about 0.001 to about 1% sweetness enhancer.

Suitable pH modifiers include, but are not limited to, hydrochloric acid, ascorbic acid, citric acid, sodium citrate, fumaric acid, sodium hydroxide, sodium bicarbonate, sodium carbonate, ammonium carbonate, and combinations thereof.

Suitable preservatives include, but are not limited to, methyl paraben, propyl paraben, benzyl alcohol, benzoic acid, sodium benzoate, sorbic acid, and combinations thereof.

Suitable flavoring agents include, but are not limited to, raspberry, peppermint oil, grape flavor, menthol, spearmint oil, citrus oil, cinnamon oil, strawberry flavor, cherry flavor, raspberry flavor, orange oil, lemon oil, lemon mint flavor, fruit punch flavor, and combinations thereof. In a preferred embodiment, the formulations contain fruit punch flavor, raspberry flavor, grape flavor, or lemon mint flavor.

If the formulations contain a flavoring agent, the formulations preferably contain from about 0.001 to about 1% flavoring agent. In a more preferred embodiment, the formulations contain from about 0.005 to about 0.5% of the flavoring agent.

The formulations are suitable for oral, buccal, sublingual, inhalation or intravenous/intramuscular administration. Preferably, the formulations are liquids administered orally.

Formulations Containing Lipids

In another embodiment, the invention is directed to stable pharmaceutical formulation for oral administration comprising from about 0.1 to about 40% of a cannabinoid and from about 10 to about 95% of a lipid.

In a preferred embodiment, the lipid is selected from the group consisting of sesame oil, olive oil, corn oil, sunflower oil, safflower oil, flaxseed oil, almond oil, peanut oil, walnut oil, cashew oil, castor oil, coconut oil, palm oil, soybean oil, canola oil, vegetable oil, rice bran oil, medium chain glycerides, decanoyl glycerides, octanoyl glycerides, caprylic/capric triglycerides, oleoyl polyoxyl-6 glycerides, linoleoyl polyoxyl-6 glycerides, polyglyceryl-3 dioleate, glyceryl monolinoleate, glyceryl monocaprylate, oleic acid, and a combination thereof. In a preferred embodiment, the lipid is selected from the group consisting of sesame oil, sunflower oil, soybean oil, corn oil, a mixture of decanoyl glycerides and octanoyl glycerides, and a combination thereof.

Suitable commercial sources for the lipid include Miglyol® 812N containing a proprietary mixture of decanoyl and octanoyl glycerides (fatty acid esters) and Miglyol® 810N also containing a proprietary mixture of decanoyl and octanoyl fatty acids from coconut oil (Miglyol is available from and a registered trademark of Cremer Oleo GmbH & Co.).

In yet another embodiment, the formulations contain a cannabinoid selected from group consisting of cannabinol, cannabidiol, dronabinol (delta-9-tetrahydrocannabinol), delta-8-tetrahydrocannabinol, 11-hydroxy-tetrahydrocannabinol, 11-hydroxy-delta-9-tetrahydrocannabinol, levonantradol, delta-11-tetrahydrocannabinol, tetrahydrocannabivarin, amandamide, nabilone, acids, analogs, and synthetic derivatives thereof. In a preferred embodiment, the cannabinoid is cannabidiol.

In yet another embodiment, the formulations contain cannabidiol that is substantially pure and synthetically synthesized which has a purity of greater than 98%. In a more preferred embodiment, the cannabidiol is greater than 99% pure. In an even more preferred embodiment, the cannabidiol is greater than 99.5% pure. In a most preferred embodiment, the cannabidiol formulation contains less than 0.3% delta-9-tetrahydrocannabinol.

In a preferred embodiment, the formulations contain from about 1 to about 35% of a cannabidiol. In a more preferred embodiment, the formulations contain from about 10 to about 32% cannabidiol. In a most preferred embodiment, the formulations contain from about 17 to about 29% cannabidiol.

In a preferred embodiment, the formulations contain from about 20 to about 90% of lipids. In a more preferred embodiment, the formulations contain from about 50 to about 90% lipids. In a most preferred embodiment, the formulations contain from about 60 to about 85% lipids.

In yet another embodiment, the formulations contain alcohol. The formulations can contain 0% alcohol. If the formulations contain alcohol, they can include from about 0.1 to about 20% alcohol. In a preferred embodiment, the formulations contain from about 3 to about 17% alcohol. In a more preferred embodiment, the formulations contain from about 5 to about 15% alcohol.

In another embodiment, the formulations contain an antioxidant. The formulations can contain 0% antioxidant. If the formulations contain antioxidant, they can include from about 0.01 to about 1% of an antioxidant. In a preferred embodiment, the formulations contain from about 0.02 to about 0.5% antioxidant. In a more preferred embodiment, the formulations contain from about 0.03 to about 0.1% antioxidant.

Suitable antioxidants include butylated hydroxyltoluene, butylated hydroxyl anisole, alpha-tocopherol (Vitamin E), ascorbyl palmitate, ascorbic acid, sodium ascorbate, ethylenediamino tetraacetic acid, cysteine hydrochloride, citric acid, sodium citrate, sodium bisulfate, sodium metabisulfite, lecithin, propyl gallate, sodium sulfate, and combinations thereof. In a preferred embodiment, the formulations contain alpha-tocopherol (Vitamin E), ascorbic acid, sodium ascorbate, ascorbyl palminate or combinations thereof.

Suitable sweeteners include, but are not limited to, sucrose, aspartame, saccharin, dextrose, mannitol, xylitol, and combinations thereof.

If the formulations contain a sweetener, the formulations preferably contain from about 0.1 to about 2% sweetener. In a more preferred embodiment, the formulations contain from about 0.1 to about 0.8% sweetener. In a most preferred embodiment, the formulations contain from about 0.2 to about 0.5% sweetener.

Suitable sweetness enhancers include, but are not limited to, the ammonium salt forms of crude and refined Glycyrrhizic Acid. Magnasweet® products (available from Mafco Worldwide Corporation, Magnasweet is a registered trademark of Mafco Worldwide Corporation) use the ammonium salt forms of crude and refined Glycyrrhizic Acid. Glycyrrhizic Acid is also available as a pure derivative in the sodium and potassium salt forms.

If the formulations contain a sweetness enhancer, the formulations preferably contain from about 0.001 to about 1% sweetness enhancer.

Suitable pH modifiers include, but are not limited to, hydrochloric acid, ascorbic acid, citric acid, sodium citrate, fumaric acid, sodium hydroxide, sodium bicarbonate, sodium carbonate, ammonium carbonate, and combinations thereof.

Suitable preservatives include, but are not limited to, methyl paraben, propyl paraben, benzyl alcohol, benzoic acid, sodium benzoate, sorbic acid, and combinations thereof.

Suitable flavoring agents include, but are not limited to, raspberry, peppermint oil, grape flavor, menthol, spearmint oil, citrus oil, cinnamon oil, strawberry flavor, cherry flavor, raspberry flavor, orange oil, lemon oil, lemon mint flavor, fruit punch flavor, and combinations thereof.

If the formulations contain a flavoring agent, the formulations preferably contain from about 0.01 to about 1% flavoring agent. In a more preferred embodiment, the formulations contain from about 0.005 to about 0.5% of the flavoring agent.

The formulations are suitable for oral, buccal, sublingual, inhalation or intravenous/intramuscular administration. Preferably, the formulations are liquids administered orally. Exemplary Uses of Formulations of the Present Invention (Alcohol-Containing, Alcohol-Free, and Lipid) and Synthetically Synthesized, Substantially Pure, Cannabidiol The formulations of the present invention are especially suitable for treatment of many diseases or disorders or symptoms of diseases and disorders. Further, cannabidiol which is synthetically synthesized and substantially pure will be even more effective and suitable for the treatment of diseases or symptoms of these diseases.

As first explained in U.S. Patent Application No. 62/004,495, Applicant unexpectedly created a new synthetic pathway for creating cannabidiol. This new process eliminated the need to grow cannabis in order to extract cannabidiol. Applicant's cannabidiol has a high purity level and is substantially free of Schedule I drugs, including delta-9-tetrahydrocannabinol.

Applicant chemically synthesized cannadbidiol by combining p-menthadienol and olivetol in toluene or dichloromethane or hexane with a p-toluene sulfonic acid catalyst to produce cannabidiol (see diagram below).

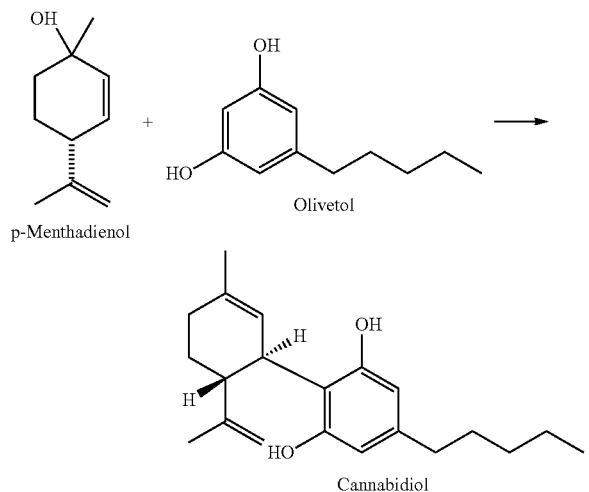

In an embodiment, the present invention is directed to methods for treating a brain tumor comprising administering the formulations of the present invention to a patient in need thereof.

In another embodiment, the present invention is directed to methods for treating a brain tumor comprising administering synthetically synthesized, substantially pure, cannabidiol to a patient in need thereof.

In an embodiment, the present invention is directed to methods for treating glioma comprising administering the formulations of the present invention to a patient in need thereof.

In another embodiment, the present invention is directed to methods for treating glioma comprising administering synthetically synthesized, substantially pure, cannabidiol to a patient in need thereof.

In an embodiment, the present invention is directed to methods for treating glioblastoma multiforme comprising administering the formulations of the present invention to a patient in need thereof.

In another embodiment, the present invention is directed to methods for treating glioblastoma multiforme comprising administering synthetically synthesized, substantially pure, cannabidiol to a patient in need thereof.

In an embodiment, the present invention is directed to methods for treating Dravet Syndrome comprising administering the formulations of the present invention to a patient in need thereof.

In another embodiment, the present invention is directed to methods for treating Dravet Syndrome comprising administering synthetically synthesized, substantially pure, cannabidiol to a patient in need thereof.

In yet another embodiment, the present invention is directed to methods for treating Lennox Gastaut Syndrome comprising administering the formulations of the present invention to a patient in need thereof.

In another embodiment, the present invention is directed to methods for treating Lennox Gastaut Syndrome comprising administering synthetically synthesized, substantially pure, cannabidiol to a patient in need thereof.

In a further embodiment, the present invention is directed to methods for treating Mycolonic Seizures comprising administering the formulations of the present invention to a patient in need thereof. In a more preferred embodiment, the alcohol-free formulations contain substantially pure cannabidiol.

In another embodiment, the present invention is directed to methods for treating Mycolonic Seizures comprising administering synthetically synthesized, substantially pure, cannabidiol to a patient in need thereof.

In a further embodiment, the present invention is directed to methods for treating Juvenile Mycolonic Epilepsy comprising administering the formulations of the present invention to a patient in need thereof. In a preferred embodiment, the alcohol-free formulations of the present invention are administered to young patients in need of treatment.

In another embodiment, the present invention is directed to methods for treating Juvenile Mycolonic Epilepsy comprising administering synthetically synthesized, substantially pure, cannabidiol to a patient in need thereof.

In an embodiment, the present invention is directed to methods for treating Refractory Epilepsy comprising administering the formulations of the present invention to a patient in need thereof. In a preferred embodiment, the alcohol-free formulations of the present invention are administered to young patients in need of treatment.

In another embodiment, the present invention is directed to methods for treating Refractory Epilepsy comprising administering synthetically synthesized, substantially pure, cannabidiol to a patient in need thereof.

In an embodiment, the present invention is directed to methods for treating juvenile spasms comprising administering the formulations of the present invention to a patient in need thereof. In a preferred embodiment, the alcohol-free formulations of the present invention are administered to young patients in need of treatment.

In another embodiment, the present invention is directed to methods for treating juvenile spasms comprising administering synthetically synthesized, substantially pure, cannabidiol to a patient in need thereof.

In an embodiment, the present invention is directed to methods for treating West Syndrome comprising administering the formulations of the present invention to a patient in need thereof. In a preferred embodiment, the alcohol-free formulations of the present invention are administered to young patients in need of treatment.

In another embodiment, the present invention is directed to methods for treating West Syndrome comprising administering synthetically synthesized, substantially pure, cannabidiol to a patient in need thereof.

In an embodiment, the present invention is directed to methods for treating infantile spasms comprising administering the formulations of the present invention to a patient in need thereof. In a preferred embodiment, the alcohol-free formulations of the present invention are administered to young patients in need of treatment.

In another embodiment, the present invention is directed to methods for treating infantile spasms comprising administering synthetically synthesized, substantially pure, cannabidiol to a patient in need thereof.

In an embodiment, the present invention is directed to methods for treating refractory infantile spasms comprising administering the formulations of the present invention to a patient in need thereof. In a preferred embodiment, the alcohol-free formulations of the present invention are administered to young patients in need of treatment.

In another embodiment, the present invention is directed to methods for treating refractory infantile spasms comprising administering synthetically synthesized, substantially pure, cannabidiol to a patient in need thereof.

In an embodiment, the present invention is directed to methods for treating tubular sclerosis complex comprising administering the formulations of the present invention to a patient in need thereof. In a preferred embodiment, the alcohol-free formulations of the present invention are administered to young patients in need of treatment.

In another embodiment, the present invention is directed to methods for treating tubular sclerosis complex comprising administering synthetically synthesized, substantially pure, cannabidiol to a patient in need thereof.

In a further embodiment, the present invention is directed to methods for treating neuropathic pain comprising administering the formulations of the present invention to a patient in need thereof. In a further embodiment, the neuropathic pain is caused by neurotoxic chemotherapy agents such as Paclitaxel, Docetaxel, Cisplatin, Oxaliplatin, Carboplatin, Vincristine, Methotrexate, Cytarabine, Fluorouracil, Ifosfamide, Cyclophosphamide, Procarbazine, etoposide, Carmustine, and Lomustine. In yet another embodiment, the neuropathic pain is caused by Paclitaxel and the patient is receiving Paclitaxel due to a diagnosis of breast, cervical, endometrial and/or ovarian cancer. In a further embodiment, the breast, cervical, endometrial and/or ovarian cancer is platinum-resistant. In another embodiment, the breast, cervical, endometrial and/or ovarian cancer is recurrent.

In another embodiment, the present invention is directed to methods for treating neuropathic pain comprising administering synthetically synthesized, substantially pure, cannabidiol to a patient in need thereof. In a further embodiment, the neuropathic pain is caused by neurotoxic chemotherapy agents such as Paclitaxel, Docetaxel, Cisplatin, Oxaliplatin, Carboplatin, Vincristine, Methotrexate, Cytarabine, Fluorouracil, Ifosfamide, Cyclophosphamide, Procarbazine, etoposide, Carmustine, and Lomustine. In yet another embodiment, the neuropathic pain is caused by Paclitaxel and the patient is receiving Paclitaxel due to a diagnosis of breast, cervical, endometrial and/or ovarian cancer. In a further embodiment, the breast, cervical, endometrial and/or ovarian cancer is platinum-resistant. In another embodiment, the breast, cervical, endometrial and/or ovarian cancer is recurrent.

In a further embodiment, the present invention is directed to methods for using cannabidiol as an analgesic comprising administering the formulations of the present invention to a patient in need thereof.

In another embodiment, the present invention is directed to methods for using cannabidiol as an analgesic comprising administering synthetically synthesized, substantially pure, cannabidiol to a patient in need thereof.

In a further embodiment, the present invention is directed to methods for treating opioid addiction withdrawal comprising administering the formulations of the present invention to a patient in need thereof. In a preferred embodiment, the alcohol-free formulations of the present invention are administered to the patient in need of treatment.

In another embodiment, the present invention is directed to methods for treating opioid addiction withdrawal comprising administering synthetically synthesized, substantially pure, cannabidiol to a patient in need thereof.

In yet another embodiment, the present invention is directed to methods for treating cocaine addiction withdrawal comprising administering the formulations of the present invention to a patient in need thereof. In a preferred embodiment, the alcohol-free formulations of the present invention are administered to the patient in need of treatment.

In another embodiment, the present invention is directed to methods for treating cocaine addiction withdrawal comprising administering synthetically synthesized, substantially pure, cannabidiol to a patient in need thereof.

In a further embodiment, the present invention is directed to methods for treating heroin addiction withdrawal comprising administering the formulations of the present invention to a patient in need thereof. In a preferred embodiment, the alcohol-free formulations of the present invention are administered to the patient in need of treatment.

In another embodiment, the present invention is directed to methods for treating heroin addiction withdrawal comprising administering synthetically synthesized, substantially pure, cannabidiol to a patient in need thereof.

In a further embodiment, the present invention is directed to methods for treating nicotine addiction withdrawal comprising administering the formulations of the present invention to a patient in need thereof. In a preferred embodiment, the alcohol-free formulations of the present invention are administered to the patient in need of treatment.

In another embodiment, the present invention is directed to methods for treating nicotine addiction withdrawal comprising administering synthetically synthesized, substantially pure, cannabidiol to a patient in need thereof.

In a further embodiment, the present invention is directed to methods for treating amphetamine addiction withdrawal comprising administering the formulations of the present invention to a patient in need thereof. In a preferred embodiment, the alcohol-free formulations of the present invention are administered to the patient in need of treatment.

In another embodiment, the present invention is directed to methods for treating amphetamine addiction withdrawal comprising administering synthetically synthesized, substantially pure, cannabidiol to a patient in need thereof.

In an embodiment, the present invention is directed to methods for treating acne comprising administering the formulations of the present invention to a patient in need thereof.

In another embodiment, the present invention is directed to methods for treating acne comprising administering synthetically synthesized, substantially pure, cannabidiol to a patient in need thereof.

In an embodiment, the present invention is directed to methods for treating Parkinson's disease comprising administering the formulations of the present invention to a patient in need thereof.

In another embodiment, the present invention is directed to methods for treating Parkinson's disease comprising administering synthetically synthesized, substantially pure, cannabidiol to a patient in need thereof.

In an embodiment, the present invention is directed to methods for treating schizophrenia comprising administering the formulations of the present invention to a patient in need thereof.

In another embodiment, the present invention is directed to methods for treating schizophrenia comprising administering synthetically synthesized, substantially pure, cannabidiol to a patient in need thereof.

In an embodiment, the present invention is directed to methods for treating social anxiety disorder comprising administering the formulations of the present invention to a patient in need thereof.

In another embodiment, the present invention is directed to methods for treating social anxiety disorder comprising administering synthetically synthesized, substantially pure, cannabidiol to a patient in need thereof.

In a further embodiment, the present invention is directed to methods for treating depression comprising administering the formulations of the present invention to a patient in need thereof.

In another embodiment, the present invention is directed to methods for treating depression comprising administering synthetically synthesized, substantially pure, cannabidiol to a patient in need thereof.

In a further embodiment, the present invention is directed to methods for treating patients encountering adverse emotional stimuli comprising administering the formulations of the present invention to a patient in need thereof.

In another embodiment, the present invention is directed to methods for treating patients encountering adverse emotional stimuli comprising administering synthetically synthesized, substantially pure, cannabidiol to a patient in need thereof.

In an embodiment, the present invention is directed to methods for treating nausea comprising administering the formulations of the present invention to a patient in need thereof.

In another embodiment, the present invention is directed to methods for treating nausea comprising administering synthetically synthesized, substantially pure, cannabidiol to a patient in need thereof.

In an embodiment, the present invention is directed to methods for treating multiple sclerosis comprising administering the formulations of the present invention to a patient in need thereof.

In another embodiment, the present invention is directed to methods for treating multiple sclerosis comprising administering synthetically synthesized, substantially pure, cannabidiol to a patient in need thereof.

In an embodiment, the invention is directed to methods for treating symptoms of cannabis use disorder comprising administering formulations of the present invention to a patient in need thereof. In a preferred embodiment, the alcohol-free formulations of the present invention are administered to the patient in need of treatment.

In another embodiment, the present invention is directed to methods for treating symptoms of cannabis use disorder comprising administering synthetically synthesized, substantially pure, cannabidiol to a patient in need thereof.

In another embodiment, the invention is directed to methods for treating symptoms of early psychosis comprising administering formulations of the present invention to a patient in need thereof.

In another embodiment, the present invention is directed to methods for treating symptoms of early psychosis comprising administering synthetically synthesized, substantially pure, cannabidiol to a patient in need thereof.

In another embodiment, the invention is directed to methods for treating symptoms of Alzheimer's Disease comprising administering formulations of the present invention to a patient in need thereof.

In another embodiment, the present invention is directed to methods for treating symptoms of Alzheimer's Disease comprising administering synthetically synthesized, substantially pure, cannabidiol to a patient in need thereof.

In yet another embodiment, the invention is directed to methods for treating symptoms of post-traumatic stress disorder ("PTSD") comprising administering formulations of the present invention to a patient in need thereof.

In another embodiment, the present invention is directed to methods for treating symptoms of post-traumatic stress disorder PTSD comprising administering synthetically synthesized, substantially pure, cannabidiol to a patient in need thereof.

In an embodiment, the invention is directed to methods for treating symptoms of anxiety comprising administering formulations of the present invention to a patient in need thereof.

In another embodiment, the present invention is directed to methods for treating anxiety comprising administering synthetically synthesized, substantially pure, cannabidiol to a patient in need thereof.

In a further embodiment, the invention is directed to methods for treating symptoms of autism comprising administering formulations of the present invention to a patient in need thereof. In a preferred embodiment, the alcohol-free formulations of the present invention are administered to the patient in need of treatment.

In another embodiment, the present invention is directed to methods for treating symptoms of autism comprising administering synthetically synthesized, substantially pure, cannabidiol to a patient in need thereof.

Definitions

As used herein, a "patient" refers to a single patient and not a patient population.

As used herein, "synthetic" refers to the chemical synthesis of cannabidiol does not refer to cannabidiol that is extracted from cannabis plant material.

As used herein, "substantially pure" refers to a preparation having chromatographical purity of cannabidiol of greater than 98%, preferably greater than 98.5%, more preferably greater than 99.0%, and most preferably greater than 99.5%.

As used herein, "substantially free of delta-9-tetrahydrocannabinol" refers to a preparation of cannabidiol having less than 0.3% of delta-9-tetrahydrocannabinol as determined by HPLC. Preferably, the preparation contains less than 0.25% of delta-9-tetrahydrocannabinol, more preferably 0.2%, and most preferably less than 0.1% of delta-9-tetrahydrocannabinol.

As used herein, all numerical values relating to amounts, weights, and the like, that are defined as "about" each particular value is plus or minus 10%. For example, the phrase "about 10% w/w" is to be understood as "9% w/w to 11% w/w." Therefore, amounts within 10% of the claimed value are encompassed by the scope of the claims.

As used here, "liquid" refers to a flowable, fluid pharmaceutical formulation. This type of formulation is not a powder to solid.

All weights herein refer to % w/w or percent weight of the total formulation.

As used herein the term "effective amount" refers to the amount necessary to treat a patient in need thereof.

As used herein the term "pharmaceutically acceptable" refers to ingredients that are not biologically or otherwise undesirable in an oral dosage form.

As used herein, "qs" means a sufficient quantity of that component to reach a desired volume or concentration.

The disclosed embodiments are simply exemplary embodiments of the inventive concepts disclosed herein and should not be considered as limiting, unless the claims expressly state otherwise.

The following examples are intended to illustrate the present invention and to teach one of ordinary skill in the art how to use the formulations of the invention. They are not intended to be limiting in any way.

All claims, aspects and embodiments of the invention, and specific examples thereof, are intended to encompass equivalents thereof.

EXAMPLES

Example 1. Alcohol-Free Formulations

The formulations in Table 1 below were prepared as follows. All the solvents are purged with nitrogen before using in manufacturing. Vitamin E, methyl paraben, propyl paraben were dissolved in propylene glycol. Polyethylene glycol 400 (PEG400) and a flavoring agent were added to the propylene glycol solution and mixed thoroughly. The water phase was prepared by dissolving sucralose and sodium ascorbate in water. Next, the solutions were combined and pH adjusted using a pH modifier. The cannabinoid was added to the excipient solution and mixed until dissolved.

Synthetically synthesized, substantially pure, cannabidiol was used as the cannabinoid.

Strawberry flavor was used as the flavoring agent.

TABLE 1

Alcohol-free Formulations

| | Formulation | | | |
|---|---|---|---|---|
| | # AF1 | # AF2 | # AF3 | # AF4 |
| Cannabinoid | 32 | 32 | 32 | 32 |
| PEG400 | 28 | 28 | 27.9 | 28.4 |
| Propylene Glycol | 34 | 34 | 34 | 34 |
| Water | 6 | 6 | 6 | 6 |
| Vitamin E (Alpha-Tocopherol) | | | | 0.05 |
| Sodium Ascorbate | | | 0.1 | 0.1 |
| Methyl Paraben | | | | 0.1 |
| Propyl Paraben | | | | 0.02 |
| Sucralose | | | | 0.05 |
| Flavoring | | | | 0.3 |
| pH adjustment | None | pH adjusted to 6 to 7 | pH adjusted to 6 to 7 | pH adjusted to 6 to 7 |
| Final pH of formulation | 8.7 | 6.7 | 6.4 | 6.6 |

Example 2. Stability of Alcohol-Free Formulations

The formulations listed in Table 1 were subjected to stability at 55° C.±2° C., 40° C.±2° C. under 75%±5% relative humidity, and 25° C.±2° C. under 60%±5% relative humidity. Stability of the formulations was analyzed at specified time points by evaluating for their potency (assay value) and impurity levels. Assay and impurities were detected using high-performance liquid chromatography with an ultraviolet detector. The assay was performed at 228 nm and indicated as a % of initial concentration. For all impurities, analysis was performed at 228 nm and expressed as a % area. Amounts of particular impurities are listed in Tables 2 to 13 as a percentage of area of each formulation along with amount of total impurities. Relative retention time (RRT) is given for each impurity.

TABLE 2

Stability Data for Cannabidiol Oral Solution Formulation # AF1 stored at 55° C. ± 2° C.

| 55° C. - Formulation # AF1 | RRT | 0 Week | 1 Week | 2 Weeks | 3 Weeks | 4 Weeks |
|---|---|---|---|---|---|---|
| Assay (% of initial concentration) | | 100.00 | 97.11 | 97.30 | 94.47 | 87.91 |
| % Cis-cannabidiol | 1.440 | 0.01 | 0.02 | 0.02 | 0.02 | 0.02 |
| % Delta-9-tetrahydrocannabinol | 1.729 | ND | ND | 0.01 | ND | 0.02 |
| % Trans-(1R,6R)-3'-methyl-cannabidiol | 1.840 | 0.05 | 0.03 | 0.03 | 0.03 | 0.02 |
| % Unknown Impurity | 0.328 | ND | BQL | BQL | BQL | 0.06 |
| | 0.345 | ND | BQL | BQL | BQL | 0.07 |
| | 0.385 | ND | BQL | BQL | BQL | 0.05 |
| | 0.404 | ND | 0.08 | 0.13 | 0.23 | 0.38 |
| | 0.460 | ND | 0.05 | 0.07 | 0.10 | 0.17 |
| | 0.486 | ND | 0.42 | 0.65 | 1.23 | 2.73 |
| | 0.505 | BQL | 0.22 | 0.22 | 0.19 | ND |
| | 0.526 | ND | 0.10 | 0.14 | 0.13 | 0.17 |
| | 0.610 | ND | ND | BQL | 0.05 | 0.08 |
| | 0.702 | ND | BQL | BQL | 0.07 | 0.08 |
| | 0.742 | ND | BQL | BQL | 0.05 | 0.07 |
| | 0.774 | 0.07 | 0.06 | 0.06 | ND | ND |
| | 0.796 | ND | 0.58 | 1.04 | 2.13 | 3.80 |
| | 0.830 | BQL | 0.31 | 0.39 | 0.59 | 0.87 |

TABLE 2-continued

Stability Data for Cannabidiol Oral Solution Formulation # AF1 stored at 55° C. ± 2° C.

| 55° C. - Formulation # AF1 | RRT | 0 Week | 1 Week | 2 Weeks | 3 Weeks | 4 Weeks |
|---|---|---|---|---|---|---|
| | 0.933 | ND | BQL | 0.06 | 0.17 | 0.37 |
| | 1.881 | ND | 0.06 | 0.09 | 0.06 | 0.06 |
| | 2.025 | ND | BQL | BQL | 0.34 | 0.39 |
| | 2.291 | ND | 0.06 | ND | ND | ND |
| Total Impurities (% Area) | | 0.13 | 1.99 | 2.91 | 5.39 | 9.41 |

ND—Not Detected
BQL—Below Quantification Limit, for unknown impurity only

TABLE 3

Stability Data for Cannabidiol Oral Solution Formulation # AF2 stored at 55° C. ± 2° C.

| 55° C. - Formulation # AF2 | RRT | 0 Week | 1 Week | 2 Weeks | 3 Weeks | 4 Weeks |
|---|---|---|---|---|---|---|
| Assay (% of initial concentration) | | 100.00 | 100.31 | 99.90 | 95.25 | 96.85 |
| % Cis-cannabidiol | 1.440 | 0.01 | 0.01 | 0.01 | 0.01 | 0.01 |
| % Delta-9-tetrahydrocannabinol | 1.730 | ND | ND | 0.01 | 0.03 | 0.06 |
| % Trans-(1R,6R)-3'-methyl-cannabidiol | 1.840 | 0.05 | 0.07 | 0.05 | 0.05 | 0.04 |
| % Unknown Impurity | 0.340 | ND | BQL | BQL | 0.05 | 0.07 |
| | 0.404 | ND | BQL | BQL | BQL | 0.08 |
| | 0.462 | ND | BQL | BQL | BQL | 0.05 |
| | 0.486 | ND | BQL | 0.22 | 0.35 | 0.94 |
| | 0.506 | ND | 0.07 | 0.13 | 0.15 | ND |
| | 0.584 | ND | BQL | BQL | 0.05 | 0.11 |
| | 0.776 | 0.07 | 0.07 | 0.06 | 0.05 | ND |
| | 0.795 | ND | BQL | 0.30 | 0.50 | 1.09 |
| | 0.830 | BQL | BQL | 0.10 | 0.14 | 0.22 |
| | 0.932 | ND | BQL | 0.07 | 0.10 | 0.18 |
| | 2.034 | ND | ND | BQL | 0.09 | BQL |
| Total Impurities (% Area) | | 0.13 | 0.22 | 0.95 | 1.57 | 2.85 |

ND—Not Detected
BQL—Below Quantification Limit, for unknown impurity only

TABLE 4

Stability Data for Cannabidiol Oral Solution Formulation # AF3 stored at 55° C. ± 2° C.

| 55° C. - Formulation # AF3 | RRT | 0 Week | 1 Week | 2 Weeks | 3 Weeks | 4 Weeks |
|---|---|---|---|---|---|---|
| Assay (% of initial concentration) | | 100.00 | 99.25 | 98.60 | 98.28 | 96.12 |
| % Cis-cannabidiol | 1.440 | 0.01 | 0.01 | 0.01 | 0.01 | 0.01 |
| % Delta-9-tetrahydrocannabinol | 1.736 | ND | ND | ND | 0.01 | 0.02 |
| % Trans-(1R,6R)-3'-methyl-cannabidiol | 1.840 | 0.05 | 0.05 | 0.05 | 0.05 | 0.05 |
| % Unknown Impurity | 0.484 | ND | ND | ND | BQL | 0.14 |
| | 0.502 | ND | BQL | BQL | 0.05 | 0.09 |
| | 0.775 | 0.06 | 0.09 | 0.10 | 0.06 | 0.05 |
| | 0.793 | ND | ND | ND | 0.06 | 0.27 |
| | 0.830 | BQL | BQL | BQL | BQL | 0.06 |
| | 0.951 | ND | BQL | ND | BQL | 0.05 |
| | 1.158 | ND | 0.06 | 0.08 | 0.12 | 0.05 |
| Total Impurities (% Area) | | 0.12 | 0.21 | 0.24 | 0.36 | 0.79 |

ND—Not Detected
BQL—Below Quantification Limit, for unknown impurity only

TABLE 5

Stability Data for Cannabidiol Oral Solution Formulation # AF4 stored at 55° C. ± 2° C.

| 55° C. - Formulation # AF4 | RRT | 0 Week | 1 Week | 2 Weeks | 3 Weeks | 4 Weeks |
|---|---|---|---|---|---|---|
| Assay (% of initial concentration) | | 100.00 | 100.92 | 99.27 | 100.16 | 98.10 |
| % Cis-cannabidiol | 1.440 | 0.01 | 0.01 | 0.01 | 0.01 | 0.01 |
| % Trans-(1R,6R)-3'-methyl-cannabidiol | 1.840 | 0.05 | 0.05 | 0.05 | 0.06 | 0.07 |
| % Unknown Impurity | 0.403 | ND | BQL | BQL | BQL | 0.06 |
| | 0.485 | ND | BQL | 0.06 | 0.18 | 0.38 |
| | 0.505 | ND | BQL | 0.05 | 0.08 | 0.12 |
| | 0.524 | ND | ND | BQL | BQL | 0.07 |
| | 0.776 | 0.07 | 0.08 | 0.05 | 0.06 | ND |
| | 0.794 | ND | ND | 0.07 | 0.31 | 0.70 |
| | 0.822 | ND | ND | BQL | 0.10 | 0.15 |
| | 0.931 | ND | ND | ND | BQL | 0.06 |
| | 1.159 | ND | BQL | 0.08 | 0.10 | ND |
| | 1.774 | ND | ND | ND | 0.05 | 0.11 |
| Total Impurities (% Area) | | 0.13 | 0.14 | 0.37 | 0.95 | 1.73 |

ND—Not Detected
BQL—Below Quantification Limit, for unknown impurity only

TABLE 6

Stability Data for Cannabidiol Oral Solution Formulation # AF1 stored at 40° C. ± 2° C. under 75% ± 5% relative humidity

| 40° C. - Formulation # AF1 | RRT | 0 Week | 2 Weeks | 4 Weeks |
|---|---|---|---|---|
| Assay (% of initial concentration) | | 100.00 | 100.18 | 95.64 |
| % Cis-cannabidiol | 1.440 | 0.01% | 0.01% | 0.01% |
| % Trans-(1R,6R)-3'-methyl-cannabidiol | 1.846 | 0.05% | 0.05% | 0.03% |
| % Unknown Impurity | 0.404 | ND | BQL | 0.12% |
| | 0.460 | ND | 0.07% | 0.08% |
| | 0.486 | ND | 0.23% | 0.87% |
| | 0.505 | BQL | 0.30% | 0.30% |
| | 0.526 | ND | 0.05% | 0.14% |
| | 0.702 | ND | BQL | 0.06% |
| | 0.774 | 0.07% | 0.07% | ND |
| | 0.796 | ND | 0.25% | 1.31% |
| | 0.830 | BQL | 0.12% | 0.44% |
| | 0.931 | ND | ND | 0.06% |
| Total Impurities (% Area) | | 0.13% | 1.15% | 3.42% |

ND—Not Detected
BQL—Below Quantification Limit, for unknown impurity only

TABLE 7

Stability Data for Cannabidiol Oral Solution Formulation # AF2 stored at 40° C. ± 2° C. under 75% ± 5% relative humidity

| 40° C. - Formulation # AF2 | RRT | 0 Week | 2 Weeks | 4 Weeks |
|---|---|---|---|---|
| Assay (% of initial concentration) | | 100.00 | 100.08 | 98.77 |
| % Cis-cannabidiol | 1.442 | 0.01% | 0.01% | 0.01% |
| % Trans-(1R,6R)-3'-methyl-cannabidiol | 1.848 | 0.05% | 0.05% | 0.04% |
| % Unknown Impurity | 0.484 | ND | ND | 0.08% |
| | 0.506 | ND | BQL | 0.11% |
| | 0.776 | 0.07% | 0.07% | 0.06% |
| | 0.794 | ND | ND | 0.09% |
| | 0.830 | BQL | BQL | 0.05% |
| Total Impurities (% Area) | | 0.13% | 0.13% | 0.44% |

ND—Not Detected
BQL—Below Quantification Limit, for unknown impurity only

TABLE 8

Stability Data for Cannabidiol Oral Solution Formulation #AF3 stored at 40° C. ± 2° C. under 75% ± 5% relative humidity

| 40° C. - Formulation # AF3 | RRT | 0 Week | 2 Week | 4 Week |
|---|---|---|---|---|
| Assay (% of initial concentration) | | 100.00 | 98.47 | 96.90 |
| % Cis-cannabidiol | 1.442 | 0.01% | 0.01% | 0.01% |
| % Trans-(1R,6R)-3'-methyl-cannabidiol | 1.846 | 0.05% | 0.05% | 0.05% |
| % Unknown Impurity | 0.775 | 0.06% | 0.08% | 0.10% |
| | 1.160 | ND | ND | 0.05% |
| Total Impurities (% Area) | | 0.12% | 0.14% | 0.21% |

ND—Not Detected

TABLE 9

Stability Data for Cannabidiol Oral Solution Formulation # AF4 stored at 40° C. ± 2° C. under 75% ± 5% relative humidity

| 40° C. - Formulation # AF4 | RRT | 0 Week | 2 Weeks | 4 Weeks |
|---|---|---|---|---|
| Assay (% of initial concentration) | | 100.00 | 99.63 | 99.50 |
| % Cis-cannabidiol | 1.437 | 0.01% | 0.01% | 0.01% |
| % Trans-(1R,6R)-3'-methyl-cannabidiol | 1.840 | 0.05% | 0.05% | 0.06% |
| % Unknown Impurity | 0.776 | 0.07% | 0.07% | 0.08% |
| Total Impurities (% Area) | | 0.13% | 0.13% | 0.15% |

TABLE 10

Stability Data for Cannabidiol Oral Solution Formulation # AF1 stored at 25° C. ± 2° C. under 60% ± 5% relative humidity

| 25° C. - Formulation # AF1 | RRT | 0 Week | 4 Weeks |
|---|---|---|---|
| Assay (% of initial concentration) | | 100.00 | 101.24 |
| % Cis-cannabidiol | 1.440 | 0.01% | 0.01% |
| % Trans-(1R,6R)-3'-methyl-cannabidiol | 1.846 | 0.05% | 0.04% |
| % Unknown Impurity | 0.459 | ND | 0.09% |
| | 0.483 | ND | 0.11% |
| | 0.505 | BQL | 0.27% |
| | 0.774 | 0.07% | 0.06% |

TABLE 10-continued

Stability Data for Cannabidiol Oral Solution Formulation # AF1 stored at 25° C. ± 2° C. under 60% ± 5% relative humidity

| 25° C. - Formulation # AF1 | RRT | 0 Week | 4 Weeks |
|---|---|---|---|
| | 0.796 | ND | 0.10% |
| | 0.836 | BQL | 0.06% |
| Total Impurities (% Area) | | 0.13% | 0.74% |

ND—Not Detected
BQL—Below Quantification Limit, for unknown impurity only

TABLE 11

Stability Data for Cannabidiol Oral Solution Formulation # AF2 stored at 25° C. ± 2° C. under 60% ± 5% relative humidity

| 25° C. - Formulation # AF2 | RRT | 0 Week | 4 Weeks |
|---|---|---|---|
| Assay (% of initial concentration) | | 100.00 | 100.22 |
| % Cis-cannabidiol | 1.442 | 0.01% | 0.01% |
| % Trans-(1R,6R)-3'-methyl-cannabidiol | 1.848 | 0.05% | 0.05% |
| % Unknown Impurity | 0.776 | 0.07% | 0.07% |
| Total Impurities (% Area) | | 0.13% | 0.13% |

TABLE 12

Stability Data for Cannabidiol Oral Solution Formulation # AF3 stored at 25° C. ± 2° C. under 60% ± 5% relative humidity

| 25° C. - Formulation # AF3 | RRT | 0 Week | 4 Weeks |
|---|---|---|---|
| Assay (% of initial concentration) | | 100.00 | 97.52 |
| % Cis-cannabidiol | 1.442 | 0.01% | 0.01% |
| % Trans-(1R,6R)-3'-methyl-cannabidiol | 1.846 | 0.05% | 0.05% |
| % Unknown Impurity | 0.775 | 0.06% | 0.08% |
| Total Impurities (% Area) | | 0.12% | 0.14% |

TABLE 13

Stability Data for Cannabidiol Oral Solution Formulation # AF4 stored at 25° C. ± 2° C. under 60% ± 5% relative humidity

| 25° C. - Formulation # AF4 | RRT | T = 0 | 4 Weeks |
|---|---|---|---|
| Assay (% of initial concentration) | | 100.00 | 99.26 |
| % Cis-cannabidiol | 1.437 | 0.01% | 0.01% |
| % Trans-(1R,6R)-3'-methyl-cannabidiol | 1.840 | 0.05% | 0.06% |
| % Unknown Impurity | 0.776 | 0.07% | 0.07% |
| Total Impurities (% Area) | | 0.13% | 0.14% |

Control formulation (#AF1) showed significant increase in levels of total impurities and decrease in the assay value. Adjusting the pH of formulation (#AF2) in the range of from about 6 to about 7 increased the stability of the formulation in comparison to control formulation. This illustrates the critical role that pH plays in cannabinoid formulations' stability. Applicant determined that the pH should be from about 6 to about 7 for optimal stability. Addition of antioxidants along with pH adjustment further increased the stability of the cannabinoid formulation. For example, formulations #AF3 and #AF4, containing antioxidant(s) and pH modifiers, showed excellent stability for four weeks regardless of temperature and humidity conditions.

Example 3. Alcohol Formulations

The formulations in Tables 14 and 15 below were prepared as follows. All the solvents were purged with nitrogen before using in manufacturing. Vitamin E, ascorbyl palmitate, methyl paraben, propyl paraben, sucralose were dissolved in ethanol. propylene glycol, polyethylene glycol 400, glycerol, flavoring agent, and water were added to the solution and mixed thoroughly. Then, if applicable, the pH of the solution was adjusted using a pH modifier. The cannabinoid was added to the excipient solution and mixed until completely dissolved.

Synthetically synthesized, substantially pure, cannabidiol was used as the cannabinoid. Strawberry flavor was used as the flavoring agent.

TABLE 14

Formulations with Alcohol

| | Formulation | | | |
|---|---|---|---|---|
| | # A5 | # A6 | # A7 | # A8 |
| Cannabinoid | 9.1 | 9.1 | 9.1 | 8.8 |
| Polyethylene glycol 400 | 3 | 3 | 3 | 3 |
| Propylene Glycol | 7.5 | 7.5 | 7.5 | 7.5 |
| Ethanol | 50.3 | 50.2 | 50.2 | 49.7 |
| Water | 30 | 30 | 30 | 30.5 |
| Vitamin E (Alpha-Tocopherol) | | 0.05 | 0.05 | 0.05 |
| Ascorbyl Palmitate | | 0.1 | 0.1 | 0.1 |
| Sucralose | 0.05 | 0.05 | 0.05 | 0.05 |
| Methyl Paraben | 0.02 | 0.02 | 0.02 | 0.02 |
| Propyl Paraben | 0.02 | 0.02 | 0.02 | 0.02 |
| Flavoring | | | | 0.3 |
| pH adjustment | None | None | pH adjusted to 6 to 7 | pH adjusted to 6 to 7 |
| Final pH of formulation | 6.06 | 4.9 | 6.5 | 6.4 |

TABLE 15

Additional Formulations with Alcohol

| Formulation | # A9 | # A10 |
|---|---|---|
| Cannabinoid | 32 | 32 |
| Polyethylene glycol 400 | 18.8 | 23.8 |
| Propylene Glycol | 39 | 39 |
| Glycerol | 5 | |
| Ethanol | 5 | 5 |
| Vitamin E (Alpha Tocopherol) | 0.05 | 0.05 |
| Ascorbyl Palmitate | 0.1 | 0.1 |
| Sucralose | 0.05 | 0.05 |
| Methyl Paraben | 0.02 | 0.02 |
| Propyl Paraben | 0.02 | 0.02 |

Example 4. Stability of Formulations with Alcohol

The formulations listed in Table 14 and Table 15 were subjected to stability at 25° C.±2° C. under 60%±5% relative humidity and 40° C.±2° C. under 75%±5% relative humidity. Stability of the formulations was analyzed at specified time points by evaluating for their potency (assay value) and impurity levels. Assay and impurities were detected using high-performance liquid chromatography with an ultraviolet detector. The assay was performed at 228 nm and indicated as a % of initial concentration. For all impurities, analysis was performed at 228 nm and expressed as a % area. Amounts of particular impurities are listed in Table 16 to 22 as a percentage of area of each formulation along with amount of total impurities. Relative retention time (RRT) is given for each impurity.

TABLE 16

Stability Data for Cannabidiol Oral Solution Formulation # A5 stored at 25° C. ± 2° C. under 60% ± 5% relative humidity

| 25° C. - Formulation # A5 | RRT | 0 Month | 3 Months | 6 Months | 9 Months | 12 Months |
|---|---|---|---|---|---|---|
| Assay (% of initial concentration) | | 100.00 | 92.97 | 83.87 | 77.31 | 68.92 |
| % Cannabinol | 1.400 | ND | ND | ND | 0.01 | ND |
| % Cis-cannabidiol | 1.455 | 0.01 | 0.01 | 0.01 | 0.02 | 0.02 |
| % Delta-9-tetrahydrocannabinol | 1.761 | ND | ND | 0.01 | 0.15 | 0.17 |
| % Unknown Impurity | 0.319 | ND | 0.08 | 0.18 | 0.34 | 0.39 |
| | 0.337 | ND | BQL | BQL | BQL | 0.05 |
| | 0.370 | ND | BQL | 0.07 | 0.08 | 0.08 |
| | 0.389 | ND | 0.11 | 0.24 | 0.42 | 0.54 |
| | 0.448 | ND | 0.18 | 0.23 | 0.24 | 0.25 |
| | 0.479 | ND | 0.78 | 1.65 | 2.66 | 3.49 |
| | 0.494 | ND | 0.50 | 0.72 | 0.82 | 0.88 |
| | 0.522 | ND | 0.05 | BQL | BQL | BQL |
| | 0.600 | ND | BQL | 0.05 | 0.09 | 0.15 |
| | 0.678 | ND | BQL | 0.10 | 0.16 | 0.21 |
| | 0.697 | ND | BQL | 0.08 | 0.08 | 0.09 |
| | 0.713 | ND | ND | ND | 0.06 | 0.10 |
| | 0.770 | 0.05 | ND | ND | ND | ND |
| | 0.790 | ND | 0.99 | 2.28 | 4.19 | 5.55 |
| | 0.819 | ND | 0.39 | 0.87 | 1.44 | 1.97 |
| | 0.930 | ND | 0.05 | 0.21 | 0.38 | 0.56 |
| | 1.189 | ND | ND | ND | BQL | 0.09 |
| | 2.053 | ND | 0.07 | ND | BQL | 0.14 |
| | 3.192 | ND | ND | ND | ND | 0.09 |
| | 3.256 | ND | ND | ND | 0.08 | 0.08 |
| | 3.650 | ND | ND | ND | ND | 0.13 |
| Total Impurities (% Area) | | 0.06 | 3.21 | 6.70 | 11.22 | 15.03 |

ND—Not Detected
BQL—Below Quantification Limit, for unknown impurity only

TABLE 17

Stability Data for Cannabidiol Oral Solution Formulation # A6 stored at 25° C. ± 2° C. under 60% ± 5% relative humidity

| 25° C. - Formulation # A6 | RRT | 0 Month | 3 Months | 6 Months | 9 Months | 12 Months |
|---|---|---|---|---|---|---|
| Assay (% of initial concentration) | | 100.00 | 97.49 | 94.25 | 91.14 | 87.53 |
| % Cannabinol | 1.400 | ND | ND | ND | 0.01 | ND |
| % Cis-cannabidiol | 1.455 | 0.01 | 0.01 | 0.01 | 0.01 | ND |
| % Delta-9-tetrahydrocannabinol | 1.761 | ND | 0.06 | 0.23 | 0.68 | 0.82 |
| % Unknown Impurity | 0.390 | ND | BQL | 0.05 | 0.10 | 0.14 |
| | 0.479 | ND | BQL | 0.08 | 0.17 | 0.25 |
| | 0.496 | ND | 0.20 | 0.87 | 1.80 | 2.41 |
| | 0.577 | ND | BQL | BQL | 0.08 | 0.10 |
| | 0.721 | ND | ND | BQL | BQL | 0.05 |
| | 0.770 | 0.05 | 0.05 | BQL | BQL | BQL |
| | 0.790 | ND | 0.05 | 0.11 | 0.25 | 0.43 |
| | 0.834 | BQL | BQL | BQL | 0.05 | 0.07 |
| | 0.961 | ND | 0.06 | 0.33 | 0.71 | 0.97 |
| | 1.197 | ND | ND | ND | ND | 0.06 |
| | 1.869 | BQL | BQL | BQL | 0.06 | 0.27 |
| | 2.066 | ND | 0.07 | 0.42 | 0.59 | 0.86 |
| | 3.247 | ND | ND | ND | 0.07 | 0.08 |
| | 3.655 | ND | ND | ND | ND | 0.11 |
| Total Impurities (% Area) | | 0.06 | 0.50 | 2.10 | 4.58 | 6.62 |

ND—Not Detected
BQL—Below Quantification Limit, for unknown impurity only

TABLE 18

Stability Data for Cannabidiol Oral Solution Formulation # A7 stored at 25° C. ± 2° C. under 60% ± 5% relative humidity

| 25° C. - Formulation # A7 | RRT | 0 Month | 3 Months | 6 Months | 9 Months | 12 Months |
|---|---|---|---|---|---|---|
| Assay (% of initial concentration) | | 100.00 | 98.69 | 96.52 | 96.30 | 96.54 |
| % Cis-cannabidiol | 1.455 | 0.01 | 0.01 | 0.01 | 0.01 | 0.01 |
| % Delta-9-tetrahydrocannabinol | 1.761 | ND | 0.01 | 0.02 | 0.03 | 0.05 |
| % Unknown Impurity | 0.479 | ND | BQL | BQL | BQL | 0.07 |
| | 0.495 | ND | BQL | 0.06 | 0.14 | 0.20 |
| | 0.770 | 0.05 | 0.05 | 0.05 | 0.05 | BQL |
| | 0.793 | ND | BQL | 0.06 | 0.06 | 0.10 |
| | 0.958 | ND | ND | ND | BQL | 0.06 |
| | 1.160 | ND | BQL | 0.05 | BQL | 0.05 |
| | 1.883 | ND | ND | ND | ND | 0.06 |
| | 2.057 | ND | ND | BQL | BQL | 0.06 |
| | 3.652 | ND | ND | ND | ND | 0.05 |
| Total Impurities (% Area) | | 0.06 | 0.07 | 0.25 | 0.29 | 0.71 |

ND—Not Detected
BQL—Below Quantification Limit, for unknown impurity only

TABLE 19

Stability Data for Cannabidiol Oral Solution Formulation # A8 stored at 25° C. ± 2° C. under 60% ± 5% relative humidity

| 25° C. - Formulation # A8 | RRT | 0 Month | 3 Months | 6 Months |
|---|---|---|---|---|
| Assay (% of initial concentration) | | 100.00 | 100.51 | 100.14 |
| % Cis-cannabidiol | 1.454 | 0.04 | 0.04 | 0.04 |
| % Delta-9-tetrahydrocannabinol | 1.762 | 0.03 | 0.04 | 0.05 |
| % Unknown Impurity | 0.501 | BQL | BQL | 0.07 |
| | 1.162 | ND | BQL | 0.07 |
| | 1.198 | ND | ND | 0.05 |
| Total Impurities (% Area) | | 0.07 | 0.08 | 0.28 |

ND—Not Detected
BQL—Below Quantification Limit, for unknown impurity only

TABLE 20

Stability Data for Cannabidiol Oral Solution Formulation # A7 stored at 40° C. ± 2° C. under 75% ± 5% relative humidity

| 40° C. - Formulation # A7 | RRT | 0 Month | 3 Months | 6 Months |
|---|---|---|---|---|
| Assay (% of initial concentration) | | 100.00 | 95.22 | 89.72 |
| % Cis-cannabidiol | 1.451 | 0.01 | 0.01 | 0.01 |
| % Delta-9-tetrahydrocannabinol | 1.753 | 0.01 | 0.06 | 0.16 |
| % Unknown Impurity | 0.390 | ND | 0.05 | 0.15 |
| | 0.450 | ND | BQL | 0.06 |
| | 0.476 | BQL | 0.23 | 0.75 |
| | 0.501 | BQL | 0.30 | 0.80 |
| | 0.609 | ND | BQL | 0.05 |
| | 0.675 | ND | BQL | 0.05 |
| | 0.772 | 0.05 | BQL | ND |
| | 0.791 | ND | 0.36 | 1.35 |
| | 0.830 | BQL | 0.12 | 0.37 |
| | 0.934 | ND | BQL | 0.25 |
| | 0.958 | ND | BQL | 0.18 |
| | 1.333 | ND | ND | 0.05 |
| | 1.982 | ND | ND | 0.17 |
| | 2.062 | BQL | 0.05 | 0.32 |
| | 3.253 | ND | BQL | 0.09 |
| | 3.744 | ND | ND | 0.13 |
| Total Impurities (% Area) | | 0.07 | 1.18 | 4.94 |

ND—Not Detected
BQL—Below Quantification Limit, for unknown impurity only

TABLE 21

Stability Data for Cannabidiol Oral Solution Formulation # A8 stored at 40° C. ± 2° C. under 75% ± 5% relative humidity

| 40° C. - Formulation # A8 | RRT | 0 Month | 3 Months | 6 Months |
|---|---|---|---|---|
| Assay (% of initial concentration) | | 100.00 | 96.57 | 92.84 |
| % Cis-cannabidiol | 1.454 | 0.04 | 0.03 | 0.03 |
| % Delta-9-tetrahydrocannabinol | 1.762 | 0.03 | 0.13 | 0.62 |
| % Unknown Impurity | 0.392 | ND | 0.06 | 0.14 |
| | 0.478 | ND | 0.22 | 0.64 |
| | 0.501 | BQL | 0.41 | 0.84 |
| | 0.610 | ND | BQL | 0.05 |
| | 0.670 | ND | BQL | 0.05 |
| | 0.792 | ND | 0.38 | 1.15 |
| | 0.821 | ND | 0.12 | 0.30 |
| | 0.931 | ND | 0.05 | 0.19 |
| | 0.956 | ND | 0.09 | 0.21 |
| | 2.068 | BQL | 0.11 | 0.23 |
| | 3.251 | ND | BQL | 0.09 |
| | 3.754 | ND | ND | 0.13 |
| Total Impurities (% Area) | | 0.07 | 1.60 | 4.67 |

ND—Not Detected
BQL—Below Quantification Limit, for unknown impurity only

TABLE 22

Stability Data for Cannabidiol Oral Solution Formulation # A9 stored at 40° C. ± 2° C. under 75% ± 5% relative humidity

| 40° C. - Formulation # A9 | RRT | 0 Week | 2 Weeks | 4 Weeks |
|---|---|---|---|---|
| Assay (% of initial concentration) | | 100.00 | 99.77 | 100.65 |
| % Cis-cannabidiol | 1.440 | 0.01 | 0.01 | 0.01 |
| % Trans-(1R,6R)-3'-methyl-cannabidiol | 1.841 | 0.05 | 0.06 | 0.05 |
| % Unknown Impurity | 0.770 | 0.06 | 0.07 | 0.08 |
| Total Impurities (% Area) | | 0.12 | 0.14 | 0.14 |

TABLE 23

Stability Data for Cannabidiol Oral Solution Formulation # A10 stored at 40° C. ± 2° C. under 75% ± 5% relative humidity

| 40° C. - Formulation # A10 | RRT | 0 Week | 2 Weeks | 4 Weeks |
|---|---|---|---|---|
| Assay (% of initial concentration) | | 100.00 | 101.25 | 100.78 |
| % Cis-cannabidiol | 1.440 | 0.01 | 0.01 | 0.01 |
| % Delta-9-tetrahydrocannabinol | 1.723 | ND | ND | 0.01 |
| % Trans-(1R,6R)-3'-methyl-cannabidiol | 1.842 | 0.05 | 0.05 | 0.05 |
| % Unknown Impurity | 0.770 | 0.07 | 0.07 | 0.06 |
| Total Impurities (% Area) | | 0.13 | 0.13 | 0.13 |

ND—Not Detected

Control formulation (#A5) showed significant increase in levels of total impurities and decrease in the assay value. The addition of antioxidants, Vitamin E and ascorbyl palmitate (see #A6) significantly increased the stability of formulation. These results illustrate the critical role of antioxidants in stabilizing cannabinoid formulations. Antioxidants Vitamin E and ascorbic acid (or its salt) show excellent synergism as ascorbic acid (or its salt) strongly inhibits the depletion of Vitamin E by regenerating it. Along with the antioxidants, the addition of pH modifiers to adjust the pH to the range of 6 to 7 resulted in exceptionally stable formulations (#A7 and #A8). The stability testing data illustrates that the pH range of from about 6 to about 7 is critical. Formulations #A9 and #A10 also showed good stability after four weeks.

Example 5: Lipid Formulations

The formulations in Table 24 were created by mixing all the solid and liquid excipients in the lipid. Cannabidiol was then dissolved. Synthetically synthesized, substantially pure, cannabidiol used as the source of the cannabinoid. Strawberry was used as the source of flavoring.

TABLE 24

Formulations with Lipids

| | Formulation | | | | | | |
|---|---|---|---|---|---|---|---|
| | # LF1 | # LF2 | # LF3 | # LF4 | # LF5 | # LF6 | # LF7 |
| Cannabinoid | 24.60 | 19.50 | 19.50 | 19.50 | 19.50 | 18.00 | 28.0 |
| Vitamin E (Alpha Tocopherol) | | 0.05 | 0.05 | 0.05 | 0.05 | 0.05 | 0.05 |
| Flavor | | 0.30 | 0.30 | 0.30 | 0.30 | 0.30 | |
| Sesame oil | 75.40 | 80.15 | 70.15 | | | | |
| Sunflower oil | | | | 80.45 | | | |
| Soybean oil | | | | | | 81.95 | |
| Corn Oil | | | | | 80.45 | | |
| A mixure of decanoyl and octanoyl glycerides (fatty acid esters) | | | | | | | 61.95 |
| Ethanol | | | 10.00 | | | | 10.00 |

Example 6: Stability of a Formulation with Lipids

Formulation #LF1 was subjected to stability at 25° C.±2° C. under 60%±5% relative humidity and 40° C.±2° C. under 75%±5% relative humidity. The stability of the formulation was analyzed at specified time points by evaluating the potency (assay value) and impurity levels. Assay and impurities were detected using high-performance liquid chromatography with an ultraviolet detector. The assay was performed at 228 nm and indicated as a % of initial concentration. For all impurities, analysis was performed at 228 nm and expressed as a % area. Amounts of particular impurities are listed in Table 25 as a percentage of area of each formulation along with amount of total impurities. Relative retention time (RRT) is given for each impurity.

TABLE 25

Three Month Stability Data for Cannabidiol Oral Solution Formulation # LF1 stored at 40° C. ± 2° C. under 75% ± 5% relative humidity and stored at 25° C. ± 2° C. under 60% ± 5% relative humidity

| Formulation # LF1 | RRT | 0 Month | 3 Months-40° C. | 3 Months-25° C. |
|---|---|---|---|---|
| Assay (% of initial concentration) | | 100.00 | 100.87 | 100.72 |
| % Cis-cannabidiol | 1.437 | 0.03 | 0.04 | 0.04 |
| % Delta 9-THC | 1.736 | 0.06 | 0.06 | 0.08 |
| % Trans-(1R,6R)-3'-methyl-cannabidiol | 1.840 | 0.02 | 0.06 | 0.02 |
| Total Impurities (% Area) | | 0.11 | 0.16 | 0.14 |

As seen in Table 25 above, formulation #LF1 with sesame oil showed good stability after 3 months at both storage conditions 25° C.±2° C./60%±5% relative humidity and 40° C.±2° C./75%±5% relative humidity.

Example 7. Paclitaxel Induced Neuropathic Pain Study

Paclitaxel is an antineoplastic agent that has activity against several types of cancer including ovary, breast, lung and the head and neck. Paclitaxel works by promoting microtubule assembly which results in neuropathy as a toxic side effect. Peripheral sensory neuropathy is the most commonly reported neurotoxic side effect of paclitaxel and it limits treatment with high and cumulative doses of paclitaxel when given alone or in combination with other neurotoxic antineoplastic agents such as cisplatin. Currently there is not a highly effective treatment for this type of pain. Therefore, there is a need for a highly effective treatment to relieve the symptoms of paclitaxel induced neuropathy.

A mouse study was conducted in order to determine the effects of cannabidiol, delta-9-tetrahydrocannabinol, and cannabidiol plus delta-9-tetrahydrocannabinol combinations to alleviate neuropathic pain caused by chemotherapy-induced peripheral neuropathy. The cannadidiol administered to the mice was substantially pure, synthetically synthesized, cannabidiol which had a purity greater than 98%.

A detailed explanation of FIG. 1 is as follows. The Y-axes represent the threshold sensitivity to mechanical stimulation, expressed as a percent of baseline sensitivity. The X-axes represent the dose of drug mg/kg administered intraperitoneally. Whereas the dotted lines represent withdrawal threshold level to mechanical stimulation of saline controls, the dashed lines represent paclitaxel-treated animals. The points along the dashed line indicate neuropathic pain while points along the dotted line represent protection from neuropathic pain. The data shown are mean+SEM sensitivity measured on Day 21 post treatment. *p<0.05 from saline control as determined by one-way ANOVA.

Specific doses of agents producing similar overt behavioral effects when added to together should produce the additive effect level.
Examples:
1) If 1.25 mg/kg cannabidiol produces 100% alleviation of pain effect and 1.25 mg/kg delta-9-tetrahydrocannabinol produces 0% effect, then those doses added together should be fully effective (as should the 2.5 mg/kg cannabidiol+2.5 mg/kg delta-9-tetrahydrocannabinol).
2) If 0.625 mg/kg cannabidiol and 0.625 delta-9-tetrahydrocannabinol produce 0% effect, then those doses in combination should be ineffective.

Applicant found (as illustrated in FIG. 1) that cannabidiol when administered alone provided the most effective level of alleviating chemotherapy-induced neuropathic pain compared to delta-9-tetrahydrocannabinol. The presence of delta-9-tetrahydrocannabinol depending on its concentration can inhibit the ability of cannabidiol to alleviate neuropathic pain. The ability of delta-9-tetrahydrocannabinol to block the pain alleviating activity of cannabidiol is also dependent of the concentration of cannabidiol. This test illustrates that a substantially pure cannabidiol formulation is highly desirable.

Example 8. Anticonvulsant Study

This study was conducted as follows according to standard models for anticonvulsant screening including the maximal electroshock test ("MES"), the minimal clonic seizure ("6 Hz") test and evaluations of toxicity ("TOX"). The data was recorded as number of animals protected (N) out of the number of animals tested (F), see Tables 26 to 29 below. The test was repeated one time. The cannabidiol administered to the mice and rats was substantially pure, synthetically synthesized, cannabidiol which had a purity greater than 98%. The cannabidiol was dissolved in 0.5% methylcellulose or a 1:1:18 ratio of ethanol:polyethoxylated castor oil:phosphate buffered saline ("PBS").

The maximal electroshock test is a model for generalized tonic-clonic seizures and provides an indication of a compound's ability to prevent seizure spread when all neuronal circuits in the brain are maximally active. These seizures are highly reproducible and are electrophysiologically consistent with human seizures. For all tests based on maximal electroshock convulsions, 60 Hz of alternating current (50 mA in mice, 150 in rats) was delivered for 0.2 s by corneal electrodes which were primed with an electrolyte solution containing an anesthetic agent (0.5% tetracaine HCl). The mice were tested at various intervals following doses of 10, 30 and 100 mg/kg of cannabidiol given by intraperitoneal injection of a volume of 0.01 mL/g. An animal was considered "protected" from maximal electroshock-induced seizures upon abolition of the hindlimb tonic extensor component of the seizure.

The minimal motor impairment test was used to determine the compounds' undesirable side effects or toxicity. During this test, the animals were monitored for overt signs of impaired neurological or muscular function. The rotorod procedure was used to disclose minimal muscular or neurological impairment. When a control mouse is placed on a rod that rotates at a speed of 6 rpm, the animal can maintain its equilibrium for long periods of time. The animal was considered toxic if it fell off this rotating rod three times during a 60 second period. In addition to minimal motor impairment, the animals may have exhibited a circular or zigzag gait, abnormal body posture and spread of the legs, tremors, hyperactivity, lack of exploratory behavior, somnolence, stupor, catalepsy, loss of placing response and changes in muscle tone.

The third test was the minimal clonic seizure (6 Hz) test. Like the maximal electroshock test, the minimal clonic seizure (6 Hz) test is used to assess a compound's efficacy against electrically induced seizures but uses a lower frequency (6 Hz) and longer duration of stimulation (3 s). Cannabidiol was pre-administered to mice via intraperitoneal injection. At varying times, individual mice (four per time point) were challenged with sufficient current delivered through corneal electrodes to elicit a psychomotor seizure in 97% of animals (32 mA for 3 s). Untreated mice will display seizures characterized by a minimal clonic phase followed by stereotyped, automatistic behaviors described originally as being similar to the aura of human patients with partial seizures. Animals not displaying this behavior are considered protected.

TABLE 26

Anticonvulsant Screening, Mice, Methylcellulose

| | | Time (Hours) | | |
|---|---|---|---|---|
| Test | Dose | 0.5 N/F | 1.0 N/F | 2.0 N/F |
| 6 HZ | 10 | 0/4 | 0/4 | 0/4 |
| 6 HZ | 30 | 0/4 | 0/4 | 0/4 |
| 6 HZ | 100 | 1/4 | 0/4 | 0/4 |

TABLE 26-continued

Anticonvulsant Screening, Mice, Methylcellulose

| Test | Dose | Time (Hours) 0.5 N/F | 1.0 N/F | 2.0 N/F |
|---|---|---|---|---|
| MES | 10 | 0/4 | 0/4 | 0/4 |
| MES | 30 | 0/4 | 0/4 | 0/4 |
| MES | 100 | 0/4 | 1/4 | 2/4 |
| TOX | 10 | 0/8 | 0/8 | 0/8 |
| TOX | 30 | 0/8 | 0/8 | 0/8 |
| TOX | 100 | 0/8 | 0/8 | 0/8 |

TABLE 27

Anticonvulsant Screening, Mice, Ethanol:Polyethoxylated castor oil:PBS

| Test | Dose | Time (Hours) 0.5 N/F | 1.0 N/F | 2.0 N/F |
|---|---|---|---|---|
| 6 HZ | 10 | 0/4 | 0/4 | 0/4 |
| 6 HZ | 30 | 0/4 | 0/4 | 0/4 |
| 6 HZ | 100 | 2/4 | 0/4 | 0/4 |
| MES | 10 | 0/4 | 0/4 | 0/4 |
| MES | 30 | 0/4 | 1/4 | 0/4 |
| MES | 100 | 0/4 | 2/4 | 1/4 |
| TOX | 10 | 0/8 | 0/8 | 0/8 |
| TOX | 30 | 0/8 | 0/8 | 0/8 |
| TOX | 100 | 0/8 | 0/8 | 0/8 |

TABLE 28

Anticonvulsant Screening, Rats, Methylcellulose

| Test | Dose | Time (Hours) 1.0 N/F | 2.0 N/F | 4.0 N/F |
|---|---|---|---|---|
| MES | 30 | 0/4 | 0/4 | 0/4 |
| MES | 100 | 0/4 | 0/4 | 0/4 |
| TOX | 30 | 0/4 | 0/4 | 0/4 |
| TOX | 100 | 0/4 | 0/4 | 0/4 |

TABLE 29

Anticonvulsant Screening, Rats, Ethanol:Polyethoxylated castor oil:PBS

| Test | Dose | Time (Hours) 1.0 N/F | 2.0 N/F | 4.0 N/F |
|---|---|---|---|---|
| MES | 30 | 0/4 | 0/4 | 0/4 |
| MES | 100 | 1/4 | 0/4 | 0/4 |
| TOX | 30 | 0/4 | 0/4 | 0/4 |
| TOX | 100 | 0/4 | 0/4 | 0/4 |

As seen in Tables 26 to 29 above, Applicant found that cannabidiol protected the mice and rats from epilepsy.

Example 9. Glioblastoma Multiforme Study

A study was conducted in order to determine the extent to which systemic administration of cannabidiol or cannabidiol plus delta-9-tetrahydrocannabinol (cannabidiol/delta-9-tetrahydrocannabinol 1:1) can inhibit glioblastoma multiforme progression and enhance the activity of temozolomide, a chemotherapy drug, in an orthotopic mouse model of glioblastoma multiforme utilizing U87 cells. It was previously suggested that the combination of cannabidiol plus delta-9-tetrahydrocannabinol is the most effective treatment for targeting tumors derived from U87 serum-derived glioblastoma multiforme cells.

The study was conducted as follows. Human U87 luciferase labeled cells were grown in Roswell Park Memorial Institute media with 10% fetal bovine serum and then harvested from dishes while in their exponential growth phase in culture with 0.1% trypsin/ethylenediaminetetraacetic acid and washed twice with serum-free Roswell Park Memorial Institute media. For the intracranial model, tumors were generated in female athymic nu/nu mice by the intracranial injection of $0.3\times10^6$ U87 cells in 4 µl of Roswell Park Memorial Institute media. Using this model, you can assess drug efficacy (in vivo imaging) as well as survival in the same group of animals. Survival studies were carried out in accordance with the National Institutes of Health's guidelines involving experimental neoplasia and our approved Institutional Animal Care and Use Committees protocol. Animals in all groups are removed from the study when they demonstrate any single sign indicative of significant tumor burden development, including hunched back, sustained decreased general activity, or a significant decrease in weight. In limited cases where tumors were able to escape the intracranial space, the mice were euthanized when the external tumors measured greater than 5 mm as assessed by callipers. Additionally, mice with tumors measuring $>500\times10^6$ radiance where removed from the study even if symptoms were not observed to assure spontaneous deaths related to seizures did not occur do to the existence of the large intracranial tumor.

The cannabinoids were dissolved in a mixture of 3% ethanol, 3% surfactant and 94% saline, and temozolomide was dissolved in 30% dimethyl sulfoxide and 70% saline. Cannabidiol that was synthetically synthesized and substantially pure was used in this study. The treatments were initiated 9 days after the injection of the tumor cells. Mice were imaged the morning before the first injection to determine initial tumor size and then groups were organized to have equal distribution of tumor size before the initiation of the first injection. Mice were treated once a day for five days with temozolomide. Mice were treated once a day, 5 days a week (Monday through Friday), with the cannabinoids until the completion of the study, except for the first week of the study where mice were injected over the weekend. All mice were administered the treatments via intraperitoneal injection. There were 12 mice per group, for a total of 72 mice. The treatment rates were as follows: cannabidiol (15 mg/kg); cannabidiol/delta-9-tetrahydrocannabinol (1:1, together @ 15 mg/kg); and temozolomide (2 mg/kg intraperitoneal injection).

Significant differences were determined using a one-way ANOVA. Bonferroni-Dunn post-hoc analyses were conducted when appropriate. Survival between groups was compared using a long-rank Mantel-Cox test. P values <0.05 defined statistical significance.

A detailed explanation of FIG. 2 is as follows. The X-axis represents the number of days after treatment and the Y-axis represents the survival rates.

As seen in FIG. 2, while 15 mg/kg of cannabidiol alone or cannabidiol/delta-9-tetrahydrocannabinol (1:1) did not inhibit glioblastoma multiforme progression, it enhanced the antitumor activity of suboptimal doses of temozolomide leading to a significant increase in survival. Further, the substantially pure, synthetically synthesized, cannabidiol produced full regression of 20% of tumors. This effect was not observed following the 1:1 cannabidiol:delta-9-tetrahydrocannabinol treatments. It was unexpected that substantially pure, synthetically synthesized, cannabidiol would have these effects because previously it was thought that a 1:1 ratio of cannabidiol (that was extracted from cannabis and not substantially pure):delta-9-tetrahydrocannabinol would produce better effects than cannabidiol alone. However, this study again illustrates the superiority of Applicant's substantially pure, synthetically synthesized, cannabidiol.

Example 10. 6 Hz Psychomotor Seizure Test

This study was conducted in order to determine the ability of synthetically-synthesized, substantially pure cannabidiol to block a psychomotor seizure induced by long-duration frequency (6 Hz) stimulation. This is a study model for therapy-resistant partial seizures.

Adult male CF1 mice (weighing 18 to 25 g) were pretreated intraperitoneally with the cannabidiol at a dose of 100 mg/kg. The cannabidiol administered to the mice was substantially pure, synthetically synthesized, cannabidiol which had a purity greater than 98%. The cannabidiol was dissolved in 0.5% methylcellulose or a 1:1:18 ratio of ethanol:polyethoxylated castor oil:PBS.

Each treatment group (n=4 mice/group) was examined for anticonvulsive effects at one of five time points (¼, ½, 1, 2, and 4 hours) following treatment with cannabidiol. Following pretreatment, each mouse received a drop of 0.5% tetracaine hydrochloride applied to each eye. The mouse was then challenged with the low-frequency (6 Hz) stimulation for 3 seconds delivered through corneal electrodes. The low-frequency, long-duration stimuli was initially delivered at 32 mA intensity. Animals were manually restrained and released immediately following the stimulations and observed for seizure activity. If the test compound was effective in the 32 mA screen, an additional assay wherein the stimulation current is increased to 44 mA is employed using the same protocol as described above. Additionally, a dose response curve can be generated at the time of peak effect (TPE) at the specific stimulation intensity.

Typically, the 6 Hz stimulation results in a seizure characterized by a minimal clonic phase that is followed by stereotyped, automatistic behaviors, including twitching of the vibrissae, and Straub-tail. Animals not displaying such behaviors were considered protected. Data was analyzed by Mann-Whitney U test, with $p<0.05$ determined to be statistically significant.

For each time group, the results are expressed as the total number of animals protected out of the number of animals tested over time (i.e., 2/4 represents 2 out of 4 mice tested were protected).

TABLE 30

ED50 Biological Response, Methylcellulose

| Test | Dose | Time (Hours) 0.5 N/F |
|---|---|---|
| 6 Hz | 30 | 0/8 |
| 6 Hz | 65 | 5/8 |
| 6 Hz | 130 | 5/8 |

TABLE 30-continued

ED50 Biological Response, Methylcellulose

| Test | Dose | Time (Hours) 0.5 N/F |
|---|---|---|
| 6 Hz | 160 | 8/16 |
| 6 Hz | 190 | 7/8 |

TABLE 31

Time to Peak Effect, Methylcellulose

| | | Time (Hours) | | | | | | |
|---|---|---|---|---|---|---|---|---|
| Test | Dose | 0.25 N/F | 0.5 N/F | 1 N/F | 2 N/F | 4 N/F | 6 N/F | 24 N/F |
| 6 Hz | 300 | 1/8 | 0/8 | 0/8 | 0/8 | 0/8 | 0/8 | 0/8 |
| 6 Hz | 500 | 1/8 | 0/8 | 0/8 | 0/8 | 0/8 | 0/8 | 2/8 |

TABLE 32

ED50 Biological Response, Ethanol:Polyethoxylated castor oil:PBS

| Test | Dose | Time | N/F |
|---|---|---|---|
| 6 Hz | 50 | 0.5 | 1/8 |
| 6 Hz | 100 | 0.5 | 1/8 |
| 6 Hz | 130 | 0.5 | 4/8 |
| 6 Hz | 170 | 0.5 | 6/8 |
| 6 Hz | 200 | 0.5 | 8/8 |
| TOX | 200 | 2 | 0/8 |
| TOX | 250 | 2 | 4/8 |
| TOX | 300 | 2 | 6/8 |
| TOX | 500 | 2 | 8/8 |

TABLE 33

Time to Peak Effect, Ethanol:Polyethoxylated castor oil:PBS

| | | Time (Hours) | | | | | | |
|---|---|---|---|---|---|---|---|---|
| Test | Dose | 0.25 N/F | 0.5 N/F | 1 N/F | 2 N/F | 4 N/F | 6 N/F | 8 N/F | 24 N/F |
| TOX | 200 | — | — | — | 0/8 | 0/8 | — | — | — |
| TOX | 250 | — | — | — | 4/8 | 3/8 | — | — | — |
| TOX | 300 | — | — | — | 6/8 | 7/8 | 4/8 | 2/8 | 1/8 |
| TOX | 500 | 0/8 | 0/8 | 0/8 | 8/8 | 8/8 | 8/8 | — | 4/7 |

As seen in Tables 30 to 33, cannabidiol in both solvents showed comparable median effective doses that inhibited seizures in 50% of animals (ED50s) in the 100 mg/kg range. While cannabidiol dissolved in the methylcellulose solvent had an ED50 of 103.75 mg/kg (95% Confidence Interval of 53.89 mg/kg to 163.84 mg/kg), it showed an ED50 of 121.52 mg/kg when dissolved in the 1:1:18 ethanol:polyethoxylated castor oil:PBS solvent (95% Confidence Interval of 87.83 mg/kg to 152.96 mg/kg). Based on the toxicity data for the cannabidiol in the methylcellulose solvent, the median toxicity dose where toxicity is observed in 50% of animals ("TD50") was determined to exceed 500 mg/kg at 0.5 hours post administration. Diarrhea at 24 hours and 1 death was reported at 24 hours at 500 mg/kg, the highest dose tested.

The TD50 was determined to be 262.37 mg/kg (95% Confidence Interval of 232.64 to 301.78) with cannabidiol dissolved in the 1:1:18 ethanol:polyethoxylated castor oil:PBS solvent. Death was reported at 24 hours at 300 mg/kg and at 6 and 24 hours for 500 mg/kg with the with the 1:1:18 ethanol:polyethoxylated castor oil:PBS solvent.

These results further illustrate that cannabidiol is likely to be effective in humans for the treatment of epilepsy and other conditions. Further, synthetically synthesized cannabidiol will likely be less toxic than cannabidiol that is derived from plants and not substantially pure.

Example 11. Maximal Electroshock Seizure and Subcutaneous Metrazol

The maximal electroshock seizure ("MES") and subcutaneous Metrazol ("sc Met") tests have been the two most widely employed preclinical seizure models for the early identification and high through-put screening of investigational anti-seizure drugs. These tests have been extremely effective in identifying new anti-seizure drugs that may be useful for the treatment of human generalized tonic-clonic seizures and generalized myoclonic seizures. The MES test provides an indication of CBD's ability to prevent seizure spread when all neuronal circuits in the brain are maximally active. The s.c. Met test detects the ability of CBD to raise the chemoconvulsant-induced seizure threshold of an animal and, thus, protect it from exhibiting a clonic, forebrain seizure.

For the MES test, 60 Hz of alternating current is delivered by corneal electrodes for 0.2 seconds. Supra-maximal seizures are elicited with a current intensity five times that necessary to evoke a threshold tonic extension seizure, i.e., 50 mA in mice and 150 mA in rats. A drop of anesthetic solution, 0.5% tetracaine hydrochloride, is placed on the eyes of each animal just before the corneal electrodes are applied to the eyes to elicit electrical stimulation. The animals are restrained by hand and released immediately following stimulation to allow observation of the entire seizure. Inhibition of the hind leg tonic extensor component is taken as the endpoint for the MES test.

A dose of Metrazol (85 mg/kg in mice) will induce convulsions in 97% of mice (CD97). The CD97 dose of Metrazol is injected into a loose fold of skin in the midline of the neck. The CD97 doses for Metrazol are confirmed annually in mice. It is administered to mice at a volume of 0.01 ml/g body weight. The animals are then placed in isolation cages to minimize stress and continuously monitored for the next 30 min for the presence or absence of a seizure. An episode of clonic spasms, approximately 3 to 5 seconds, of the fore and/or hind limbs, jaws, or vibrissae is taken as the endpoint. Animals not displaying fore and/or hind limb clonus, jaw chomping, or vibrissae twitching are considered protected.

All quantitative in vivo antiseizure/behavioral impairment studies are typically conducted at the previously determined TPE. Groups of at least 8 mice were tested with various doses of cannabidiol until at least two points are established between the limits of 100% protection or minimal toxicity and 0% protection or minimal toxicity. The dose of drug required to produce the desired endpoint in 50% of animals (ED50 or TD50) in each test, the 95% confidence interval, the slope of the regression line, and the standard error of the mean (S.E.M.) of the slope is then calculated by probit analysis.

The cannabidiol administered to the mice was substantially pure, synthetically synthesized, cannabidiol which had a purity greater than 98%. The cannabidiol was dissolved in 0.5% methylcellulose or a 1:1:18 ratio of ethanol:polyethoxylated castor oil:PBS. The maximal electric shock (MES) and subsucanteous Metrazol ("sc MET") are the most widely used preclinical seizure models for the early identification and screening of new antiepileptic drugs.

TABLE 34

ED50 Biological Response, Methylcellulose

| Test | Dose | Time | N/F |
|---|---|---|---|
| MES | 200 | 2 | 5/8 |
| MES | 250 | 2 | 4/8 |
| MES | 300 | 2 | 4/8 |
| MES | 350 | 2 | 3/8 |
| MES | 400 | 2 | 3/8 |
| MES | 450 | 2 | 6/8 |
| MES | 500 | 2 | 8/8 |
| Sc MET | 150 | 2 | 1/8 |
| Sc MET | 200 | 2 | 3/8 |
| Sc MET | 300 | 2 | 5/8 |
| Sc MET | 360 | 2 | 7/8 |
| TOX | 500 | 2 | 0/8 |

TABLE 35

Time to Peak Effect, Methylcellulose

| | | Time (Hours) | | | | |
|---|---|---|---|---|---|---|
| Test | Dose | 0.25 N/F | 0.5 N/F | 1 N/F | 2 N/F | 4 N/F |
| MES | 300 | 0/4 | 1/4 | 1/4 | 4/8 | 2/4 |
| Sc MET | 200 | 0/4 | 0/4 | 2/8 | 3/8 | — |
| TOX | 300 | 0/4 | 0/4 | 0/4 | 0/4 | 0/4 |

TABLE 36

ED50 Biological Response, Ethanol:Polyethoxylated castor oil:PBS

| Test | Dose | Time | N/F |
|---|---|---|---|
| MES | 75 | 2 | 1/8 |
| MES | 95 | 2 | 5/8 |
| MES | 120 | 2 | 7/8 |
| MES | 150 | 2 | 8/8 |
| Sc MET | 120 | 2 | 0/8 |
| Sc MET | 160 | 2 | 2/8 |
| Sc MET | 220 | 2 | 5/8 |
| Sc MET | 260 | 2 | 7/8 |
| TOX | 175 | 2 | 0/8 |
| TOX | 250 | 2 | 4/8 |
| TOX | 325 | 2 | 6/8 |
| TOX | 500 | 2 | 8/8 |

TABLE 37

Time to Peak Effect, Ethanol:Polyethoxylated castor oil:PBS

| | | Time (Hours) | | | | | | |
|---|---|---|---|---|---|---|---|---|
| Test | Dose | 0.25 N/F | 0.5 N/F | 1 N/F | 2 N/F | 4 N/F | 6 N/F | 8 N/F |
| TOX | 500 | 0/8 | 0/8 | 0/8 | 8/8 | 7/8 | 7/8 | 4/8 |

The ED50 in the MES model for cannabidiol dissolved in the methylcellulose solvent could not be calculated due to a U shaped dose response (¼ protected at 0.5 hr, ¼ at 1 hr, ⅜ at 2 hr and ⅔ at 4 hr). However, the ED50 for cannabidiol dissolved in the 1:1:18 ethanol:polyethoxlated castor oil: PBS solvent is 92.21 mg/kg (95% Confidence Interval of 78.4 mg/kg to 104.63 mg/kg).

For the MET model, the ED50 was 241.03 mg/kg (95% Confidence Interval of 182.23 to 311.87) for cannabidiol dissolved in the methylcellulose solvent and 198.51 mg/kg (95% Confidence Interval of 167.76 mg/kg to 232.58 mg/kg) for cannabidiol dissolved in the 1:1:18 ethanol:polyethoxlated castor oil:PBS solvent. Based on the toxicity data for cannabidiol dissolved in the methylcellulose solvent the TD50 was determined to exceed 500 mg/kg, the highest dose tested.

Myoclonic jerks were reported in at 1 hour with 200 mg/kg dose and at 2 hours with 360 mg/kg dose. The TD50 was determined to be 266.76 mg/kg (95% Confidence Interval of 222.28 mg/kg to 317.42 mg/kg) with the cannabidiol dissolved in the 1:1:18 ethanol:polyethoxlated castor oil: PBS solvent.

These results further illustrate that cannabidiol is likely to be effective in humans for the treatment of epilepsy and other conditions. Further, synthetically synthesized cannabidiol will likely be less toxic than cannabidiol that is derived from plants and not substantially pure.

We claim:

1. A stable pharmaceutical formulation for oral administration comprising:
   from about 8 to about 32% of cannabidiol that has a purity greater than 98% and comprises 2% or less of other cannabinoids;
   from about 3 to about 24% of a polyethylene glycol;
   from about 7.5 to about 39% of propylene glycol;
   from about 30 to about 31% of water;
   about 50% of alcohol; and
   from about 0.001 to about 1% of an antioxidant, wherein the antioxidant is alpha-tocopherol (Vitamin E),
   wherein the formulation has a pH of from about 5 to about 8 and the formulation is a liquid for oral administration.

2. The formulation of claim 1 wherein the pH is from about 6 to about 7.

3. A method for treating a disease or disorder, or a symptom of a disease or disorder, comprising administering the formulation of claim 1 to a patient in need thereof, wherein the disease or disorder is selected from the group consisting of Dravet Syndrome, Lennox Gastaut Syndrome, myoclonic seizures, juvenile myoclonic epilepsy, refractory epilepsy, schizophrenia, juvenile spasms, West syndrome, infantile spasms, refractory infantile spasms, tubular sclerosis complex, brain tumors, neuropathic pain, cannabis use disorder, post-traumatic stress disorder, anxiety, early psychosis, Alzheimer's Disease, and autism.

4. A method for assisting with withdrawal from opioids, cocaine, heroin, amphetamines or nicotine comprising administering the formulation of claim 1 to a patient in need thereof.

5. The formulation of claim 1, further comprising ascorbyl palmitate.

6. The formulation of claim 5, comprising about 0.1% ascorbyl palmitate.

7. The formulation of claim 1, comprising about 8 to about 11% of cannabidiol.

8. The formulation of claim 1, comprising about 8.8% of cannabidiol.

9. The formulation of claim 1, wherein the polyethylene glycol is PEG400.

10. The formulation of claim 1, comprising:
    about 8.8% of cannabidiol;
    3% of PEG400;
    7.5% of propylene glycol;
    about 50% of alcohol;
    30 to 31% of water;
    0.05% of alpha-tocopherol (Vitamin E); and
    0.1% of ascorbyl palmitate.

11. The formulation of claim 1, comprising:
    about 8.8% of cannabidiol;
    3% of PEG400;
    7.5% of propylene glycol;
    about 50% of alcohol;
    30 to 31% of water;
    0.05% of alpha-tocopherol (Vitamin E);
    0.1% of ascorbyl palmitate;
    0.05% of sucralose;
    0.02% of methyl paraben;
    0.02% of propyl paraben; and
    a flavoring agent.

12. The formulation of claim 1, consisting of:
    about 8.8% of cannabidiol;
    3% of PEG400;
    7.5% of propylene glycol;
    about 50% of alcohol;
    30 to 31% of water;
    0.05% of alpha-tocopherol (Vitamin E);
    0.1% of ascorbyl palmitate;
    0.05% of sucralose;
    0.02% of methyl paraben;
    0.02% of propyl paraben; and
    a flavoring agent.

* * * * *